(12) United States Patent
Cosenza et al.

(10) Patent No.: US 9,216,219 B2
(45) Date of Patent: Dec. 22, 2015

(54) ANTI-BAFFR ANTIBODY FORMULATION

(71) Applicants: Marta Cosenza, Basel (CH); Christoph Stark, Lorrach (DE)

(72) Inventors: Marta Cosenza, Basel (CH); Christoph Stark, Lorrach (DE)

(73) Assignee: Novartis AG, Basel (CH)

( * ) Notice: Subject to any disclaimer, the term of this patent is extended or adjusted under 35 U.S.C. 154(b) by 60 days.

(21) Appl. No.: 13/912,355

(22) Filed: Jun. 7, 2013

(65) Prior Publication Data

US 2013/0344088 A1 Dec. 26, 2013

Related U.S. Application Data

(60) Provisional application No. 61/658,472, filed on Jun. 12, 2012.

(51) Int. Cl.

| | | |
|---|---|---|
| *C07K 16/00* | (2006.01) | |
| *C07K 16/28* | (2006.01) | |
| *A61K 39/395* | (2006.01) | |
| *A61K 9/00* | (2006.01) | |
| *A61K 47/18* | (2006.01) | |
| *A61K 47/26* | (2006.01) | |
| *C07K 14/705* | (2006.01) | |
| *C07K 14/71* | (2006.01) | |
| *C07K 14/715* | (2006.01) | |
| *A61K 39/00* | (2006.01) | |

(52) U.S. Cl.
CPC .......... *A61K 39/39591* (2013.01); *A61K 9/0019* (2013.01); *A61K 47/183* (2013.01); *A61K 47/26* (2013.01); *C07K 16/28* (2013.01); *C07K 16/2878* (2013.01); *A61K 2039/505* (2013.01); *C07K 2317/41* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2006/0088523 A1 | 4/2006 | Andya et al. | |
| 2008/0181888 A1 * | 7/2008 | Ambrose et al. | ............ 424/133.1 |
| 2014/0186373 A1 * | 7/2014 | Cosenza et al. | ............ 424/173.1 |

FOREIGN PATENT DOCUMENTS

| | | |
|---|---|---|
| WO | 2010007082 A1 | 1/2010 |
| WO | 2012076670 A2 | 6/2012 |

OTHER PUBLICATIONS

Feng He et al. "High Throughput Thermostability Screening of Monoclonal Antibody Formulations" Journal of Pharmaceuticals Sciences, vol. 99, No. 4: 1707-1720 (Apr. 2010).

Colandene et al., "Lyophilization Cycle Development for a High-Concentration Monoclonal Antibody Formulation Lacking a Crystalline Bulking Agent" JOPS, vol. 96, No. 6: 1598-1608 (Jun. 2007).

Daugherty et al., "Formulation and Delivery Issues for Monoclonal Antibody Therapeutics" Advanced Drug Delivery Reviews 58, 686-706 (2006).

Wang, "Instability, Stabilization, and Formulation of Liquid Protein Pharmaceuticals" International Journal of Pharmaceutics 185, 129-188 (1999).

* cited by examiner

*Primary Examiner* — Bridget E Bunner

(57) ABSTRACT

Anti-BAFFR antibodies are formulated as liquid formulation comprising a high concentration of the antibody active ingredient for delivery to a patient without high levels of antibody aggregation. The aqueous pharmaceutical composition may include one or more sugars, a buffering agent, a surfactant, and/or a free amino acid.

5 Claims, No Drawings

```
SEQUENCE LISTING

<160> NUMBER OF SEQ ID NOS: 15

<210> SEQ ID NO 1
<211> LENGTH: 124
<212> TYPE: PRT
<213> ORGANISM: Homo sapiens

<400> SEQUENCE: 1

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser
        115                 120

<210> SEQ ID NO 2
<211> LENGTH: 108
<212> TYPE: PRT
<213> ORGANISM: Homo sapiens

<400> SEQUENCE: 2
```

```
Asp Ile Val Leu Thr Gln Ser Pro Ala Thr Leu Ser Leu Ser Pro Gly
1               5                  10                  15

Glu Arg Ala Thr Leu Ser Cys Arg Ala Ser Gln Phe Ile Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ser Ser Ser Arg Ala Thr Gly Val Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Leu Tyr Ser Ser Pro
                85                  90                  95

Met Thr Phe Gly Gln Gly Thr Lys Val Glu Ile Lys
            100                 105
```

```
<210> SEQ ID NO 3
<211> LENGTH: 12
<212> TYPE: PRT
<213> ORGANISM: Homo sapiens

<400> SEQUENCE: 3

Gly Asp Ser Val Ser Ser Asn Ser Ala Ala Trp Gly
1               5                  10
```

```
<210> SEQ ID NO 4
<211> LENGTH: 18
<212> TYPE: PRT
<213> ORGANISM: Homo sapiens

<400> SEQUENCE: 4

Arg Ile Tyr Tyr Arg Ser Lys Trp Tyr Asn Ser Tyr Ala Val Ser Val
1               5                  10                  15

Lys Ser
```

```
<210> SEQ ID NO 5
<211> LENGTH: 12
<212> TYPE: PRT
<213> ORGANISM: Homo sapiens

<400> SEQUENCE: 5

Tyr Asp Trp Val Pro Lys Ile Gly Val Phe Asp Ser
1               5                  10
```

```
<210> SEQ ID NO 6
<211> LENGTH: 12
<212> TYPE: PRT
<213> ORGANISM: Homo sapiens

<400> SEQUENCE: 6

Arg Ala Ser Gln Phe Ile Ser Ser Ser Tyr Leu Ser
1               5                  10
```

```
<210> SEQ ID NO 7
<211> LENGTH: 7
<212> TYPE: PRT
<213> ORGANISM: Homo sapiens

<400> SEQUENCE: 7

Gly Ser Ser Ser Arg Ala Thr
1               5
```

```
<210> SEQ ID NO 8
<211> LENGTH: 9
<212> TYPE: PRT
<213> ORGANISM: Homo sapiens

<400> SEQUENCE: 8

Gln Gln Leu Tyr Ser Ser Pro Met Thr
1               5

<210> SEQ ID NO 9
<211> LENGTH: 454
<212> TYPE: PRT
<213> ORGANISM: Homo sapiens

<400> SEQUENCE: 9

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Gly Trp Ile Arg Gln Ser Pro Gly Arg Gly Leu Glu
        35                  40                  45

Trp Leu Gly Arg Ile Tyr Tyr Arg Ser Lys Trp Tyr Asn Ser Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Tyr Asp Trp Val Pro Lys Ile Gly Val Phe Asp
            100                 105                 110

Ser Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
```

```
                        325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
                355                 360                 365
Gln Val Ser Leu Thr Cys Leu Val Lys Gly Phe Tyr Pro Ser Asp Ile
            370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
            435                 440                 445
Ser Leu Ser Pro Gly Lys
        450

<210> SEQ ID NO 10
<211> LENGTH: 215
<212> TYPE: PRT
<213> ORGANISM: Homo sapiens

<400> SEQUENCE: 10

Asp Ile Val Leu Thr Gln Ser Pro Ala Thr Leu Ser Leu Ser Pro Gly
1               5                   10                  15
Glu Arg Ala Thr Leu Ser Cys Arg Ala Ser Gln Phe Ile Ser Ser Ser
                20                  25                  30
Tyr Leu Ser Trp Tyr Gln Gln Lys Pro Gly Gln Ala Pro Arg Leu Leu
            35                  40                  45
Ile Tyr Gly Ser Ser Ser Arg Ala Thr Gly Val Pro Ala Arg Phe Ser
        50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Leu Tyr Ser Ser Pro
                85                  90                  95
Met Thr Phe Gly Gln Gly Thr Lys Val Glu Ile Lys Arg Thr Val Ala
                100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
Tyr Ala Cys Glu Val Thr His Gln Gly Leu Ser Ser Pro Val Thr Lys
            195                 200                 205
Ser Phe Asn Arg Gly Glu Cys
        210                 215

<210> SEQ ID NO 11
<211> LENGTH: 372
```

```
<212> TYPE: DNA
<213> ORGANISM: Homo sapiens

<400> SEQUENCE: 11
caggtgcagc tgcagcagag cggcccaggc ctggtcaagc cctctcagac cctgtcactg      60
acctgcgcca tttcaggcga cagcgtgagc agcaacagcg ccgcctgggg ctggatcagg     120
cagagccccg tagggggcct ggaatggctg ggcaggatct actacaggtc caagtggtac     180
aacagctacg ccgtgagcgt gaagagcagg atcaccatca ccctgacaca cagcaagaac     240
cagttctcac tgcagctcaa cagcgtgacc cccgaggaca ccgccgtgta ctactgcgcc     300
agatacgact gggtgcccaa gatcggcgtg ttcgacagct ggggccaggg caccctggtg     360
accgtgtcaa gc                                                         372

<210> SEQ ID NO 12
<211> LENGTH: 324
<212> TYPE: DNA
<213> ORGANISM: Homo sapiens

<400> SEQUENCE: 12
gatatcgtgc tgacacagag ccccgccacc ctgagcctga gcccaggcga gagggccacc      60
ctgtcctgca gggccagcca gtttatcagc agcagctacc tgtcctggta tcagcagaag     120
cccggccagg cccctagact gctgatctac ggcagtcct ctcggccac cggcgtgccc     180 gccaggttca gcggcagcgg ctccggcacc gacttcaccc tgacaatcag cagcctggag     240
cccgaggact cgccgtgta ctactgccag cagctgtaca gctcacccat gaccttcggc     300
cagggcacca aggtggagat caag                                            324

<210> SEQ ID NO 13
<211> LENGTH: 184
<212> TYPE: PRT
<213> ORGANISM: Homo sapiens

<400> SEQUENCE: 13

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
                20                  25                  30

Val Ala Cys Gly Leu Leu Arg Thr Pro Arg Pro Lys Pro Ala Gly Ala
            35                  40                  45

Ser Ser Pro Ala Pro Arg Thr Ala Leu Gln Pro Gln Glu Ser Val Gly
        50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Arg Gln Arg Arg Leu Arg Gly Ala Ser
                100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175
```

Lys Thr Ala Gly Pro Glu Gln Gln
            180

<210> SEQ ID NO 14
<211> LENGTH: 1419
<212> TYPE: DNA
<213> ORGANISM: Homo sapiens

<400> SEQUENCE: 14

| | | | | | |
|---|---|---|---|---|---|
| atggcctggg | tgtggaccct | gcccttcctg | atggccgctg | cccagtcagt | gcaggcccag | 60 |
| gtgcagctgc | agcagagcgg | cccaggcctg | gtcaagccct | cagacccct | gtcactgacc | 120 |
| tgcgccattt | caggcgacag | cgtgagcagc | aacagcgccg | cctggggctg | gatcaggcag | 180 |
| agccccggta | ggggcctgga | atggctgggc | aggatctact | acaggtccaa | gtggtacaac | 240 |
| agctacgccg | tgagcgtgaa | gagcaggatc | accatcaacc | ctgacaccag | caagaaccag | 300 |
| ttctcactgc | agctcaacag | cgtgaccccc | gaggacaccg | ccgtgtacta | ctgcgccaga | 360 |
| tacgactggg | tgcccaagat | cggcgtgttc | gacagctggg | gccagggcac | cctggtgacc | 420 |
| gtgtcaagcg | ccagcaccaa | gggcccagc | gtgttccccc | tggcccccag | cagcaagagc | 480 |
| accagcggcg | gcacagccgc | cctgggctgc | ctggtgaagg | actacttccc | cgagcccgtg | 540 |
| accgtgtcct | ggaacagcgg | agccctgacc | tccggcgtgc | acaccttccc | cgccgtgctg | 600 |
| cagagcagcg | gcctgtacag | cctgtccagc | gtggtgacag | tgcccagcag | cagcctgggc | 660 |
| acccagacct | acatctgcaa | cgtgaaccac | aagcccagca | acaccaaggt | ggacaagaga | 720 |
| gtggagccca | gagctgcga | caagacccac | acctgccccc | cctgcccagc | ccagagctg | 780 |
| ctgggcggac | cctccgtgtt | cctgttcccc | ccaagcca | aggacaccct | gatgatcagc | 840 |
| aggaccccg | aggtgacctg | cgtggtggtg | gacgtgagcc | acgaggaccc | agaggtgaag | 900 |
| ttcaactggt | acgtggacgg | cgtggaggtg | cacaacgcca | agaccaagcc | cagagaggag | 960 |
| cagtacaaca | gcacctacag | ggtggtgtcc | gtgctgaccg | tgctgcacca | ggactggctg | 1020 |
| aacggcaagg | aatacaagtg | caaggtctcc | aacaaggccc | tgccagcccc | catcgaaaag | 1080 |
| accatcagca | aggccaaggg | ccagccacgg | gagccccagg | tgtacaccct | gccccctcc | 1140 |
| cgggaggaga | tgaccaagaa | ccaggtgtcc | ctgacctgtc | tggtgaaggg | cttctacccc | 1200 |
| agcgacatcg | ccgtggagtg | ggagagcaac | ggccagcccg | agaacaacta | caagaccacc | 1260 |
| cccccagtgc | tggacagcga | cggcagcttc | ttcctgtaca | gcaagctgac | cgtggacaag | 1320 |
| tccaggtggc | agcagggcaa | cgtgttcagc | tgcagcgtga | tgcacgaggc | cctgcacaac | 1380 |
| cactacaccc | agaagagcct | gagcctgtcc | cccggcaag | | | 1419 |

<210> SEQ ID NO 15
<211> LENGTH: 705
<212> TYPE: DNA
<213> ORGANISM: Homo sapiens

<400> SEQUENCE: 15

| | | | | | |
|---|---|---|---|---|---|
| atgagcgtgc | tgacccaggt | gctggctctg | ctgctgctgt | ggctgaccgg | caccagatgc | 60 |
| gatatcgtgc | tgacacagag | ccccgccacc | ctgagcctga | gccaggcga | gagggccacc | 120 |
| ctgtcctgca | gggccagcca | gtttatcagc | agcagctacc | tgtcctggta | tcagcagaag | 180 |
| cccggccagg | cccctagact | gctgatctac | ggcagctcct | tcggcca | cggcgtgccc | 240 |
| gccaggttca | gcggcagcgg | ctccggcacc | gacttcaccc | tgacaatcag | cagcctggag | 300 |
| cccgaggact | tcgccgtgta | ctactgccag | cagctgtaca | gctcacccat | gaccttcggc | 360 |

```
cagggcacca aggtggagat caagcgtacg gtggccgctc ccagcgtgtt catcttcccc    420
cccagcgacg agcagctgaa gagcggcacc gccagcgtgg tgtgcctgct gaacaacttc    480 taccccggg  aggccaaggt gcagtggaag gtggacaacg ccctgcagag cggcaacagc    540
caggagagcg tcaccgagca ggacagcaag gactccacct acagcctgag cagcaccctg    600
accctgagca aggccgacta cgagaagcat aaggtgtacg cctgcgaggt gacccaccag    660
ggcctgtcca gccccgtgac caagagcttc aacaggggcg agtgc                    705
```

ANTI-BAFFR ANTIBODY FORMULATION

SEQUENCE LISTING

The instant application contains a Sequence Listing which has been submitted in ASCII format via EFS-Web and is hereby incorporated by reference in its entirety. Said ASCII copy, created on Sep. 3, 2013, is named PAT055133-US-NP-ST25.txt and is 14,929 bytes in size.

TECHNICAL FIELD

The present invention relates to a pharmaceutical formulation of an antibody against BAFFR (BAFF receptor), a process for the preparation thereof and uses of the formulation.

BACKGROUND

The BAFFR:BAFF pair is critically involved in the maturation of transitional B-cells, for survival and activation of mature B-cells, and for isotype class switching in response to T cell-dependent antigens. BAFF and its receptor BAFFR are also important for survival and growth of malignant B-cells. Further, BAFFR normally is not expressed on pre-B cells, but was recently shown to be expressed on human ALL (B-lineage acute lymphoblastic leukemia) cells (Parameswaran, 2010, Cancer Res. 70(11) 4346-4356). The removal of autoreactive B cells and the blockade of inappropriate survival/activation mediated by excess BAFF levels in patients suffering from autoimmune disorders or cancer represents a well-validated therapeutic goal. Thus, an anti-BAFFR antibody, in particular an antibody capable of antibody-dependent cell-mediated cytotoxicity (ADCC) and blockade of ligand binding to BAFFR may offer an effective therapeutic agent in autoimmune diseases and B cell neoplasms.

Antibodies against BAFFR are known from e.g. WO 2010/007082 and include antibodies which are characterized by comprising a $V_H$ domain with the amino acid sequence of SEQ ID NO: 1 and a $V_L$ domain with the amino acid sequence of SEQ ID NO: 2. The antibody MOR6654 is one such antibody (IgG1 kappa). It has the heavy chain amino acid sequence of SEQ ID NO: 9 and the light chain amino acid sequence of SEQ ID NO: 10. This antibody may be expressed from SEQ ID NOs: 14 and 15, preferably in a host cell which lacks fucosyltransferase, for example in a mammalian cell line with an inactive FUT8(−/−) gene, to provide a functional non-fucosylated anti-BAFFR antibody with enhanced ADCC. This antibody is referred to hereafter as MOR6654B. Alternative ways to produce non-fucosylated antibodies are known in the art.

Therapeutic antibodies are typically formulated either in aqueous form ready for parenteral administration or as lyophilisates for reconstitution with a suitable diluent prior to administration.

International Application PCT/EP2011/072248 discloses lyophilisates, which can be reconstituted to give a solution with a high concentration of the antibody active ingredient and a low level of antibody aggregation for delivery to a patient. High concentrations of antibody are useful as they reduce the dosing volume, which must be delivered to a patient. Reduced dosing volumes minimize the time taken to deliver a fixed close to the patient.

Pharmaceutical compositions formulated to contain high concentration of antibody may, however, have short shelf lives and the formulated antibodies may loose biological activity resulting from chemical and physical instabilities during the storage. Among those, aggregation, deamidation and oxidation are known to be the most common causes of antibody degradation. Further, aggregation can potentially lead to increased immune response in patients, leading to safety concerns. Thus antibody aggregation in pharmaceutical compositions must be minimized or prevented.

It is therefore an objective of the present invention to provide further and improved pharmaceutical compositions comprising anti-BAFFR antibodies, formulated such as to allow high concentration of anti-BAFFR antibodies with no or substantially no antibody aggregation.

It is another objective of the present invention to provide an anti-BAFFR antibody formulation suitable for subcutaneous administration. The advantage of subcutaneous injection is that it allows the medical practitioner to perform it in a rather short intervention with the patient. Moreover the patient can be trained to perform the subcutaneous injection by himself.

This objective is met by the pharmaceutical aqueous compositions of the present invention.

The aqueous compositions of the invention comprise high concentration of anti-BAFFR antibodies, but no or essentially no aggregated antibodies and are thus particularly suitable for subcutaneous administration.

In one embodiment, the present invention relates to aqueous compositions having a pH of 5.0-7.0 and comprising
(i) an anti-BAFFR antibody wherein the antibody has a concentration of 18-165 mg/mL, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) a stabilizer,
(iii) a buffering agent,
(iv) a surfactant, and, optionally,
(v) an amino acid.

In particular, the invention provides an aqueous composition having a pH of 5.5-6.5 and comprising
(i) an anti-BAFFR antibody wherein the antibody has a concentration of 18-165 mg/mL, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) sucrose, trehalose or mannitol as a stabilizer,
(iii) histidine, citrate or succinate as a buffering agent,
(iv) polysorbate 20, poloxamer 188 or hydroxyproyl-b-cyclodextrin as a surfactant, and, optionally,
(v) arginine as an amino acid.

In one embodiment, the aqueous composition of the invention as described herein in the various embodiments comprises the anti-BAFFR antibody in a concentration of between 20 mg/mL and 150 mg/mL, particularly of between 80 mg/mL and 150 mg/mL, particularly of between 100 mg/mL and 150 mg/mL.

In one embodiment, the aqueous composition of the invention as described herein in the various embodiments comprises a sugar as a stabilizing agent, particularly sucrose, mannitol or trehalose, in a concentration of between 80 mM and 300 mM, particularly of between 120 mM and 270 mM, particularly of between 120 mM and 220 mM.

In one embodiment, the aqueous composition of the invention as described herein in the various embodiments comprises a surfactant, particularly polysorbate 20 or poloxamer 188, in a concentration of between 0.01% and −0.1%, particularly of between 0.02% and 0.06%.

In one embodiment, the aqueous composition of the invention as described herein in the various embodiments comprises a buffering agent, particularly histidine, citrate or succinate, in a concentration of between 5 mM and 50 mM, particularly in a concentration of between 15 mM and 25 mM, particularly of between 18 mM and 22 mM, particularly 20 mM.

In one embodiment, the aqueous composition of the invention as described herein in the various embodiments comprises in addition an amino acid, particularly arginine or arginine-HCl, in a concentration of between 2 mM and 80 mM.

In one embodiment, the aqueous composition of the invention as described herein in the various embodiments comprises sucrose or trehalose in a concentration of between 110 mM and 250 mM.

In a specific embodiment, the present invention provides an aqueous composition having a pH of 5.5-6.5 and comprising
(i) an anti-BAFFR antibody wherein the antibody has a concentration of 18 mg/mL-165 mg/mL, and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 80 mM-300 mM sucrose, trehalose or mannitol as a stabilizer,
(iii) 5 mM-50 mM histidine, citrate or succinate as a buffering agent,
(iv) 0.01%-0.1% polysorbate 20 or poloxamer 188, or 1 mM-3 mM hydroxyproyl-b-cyclodextrin as a surfactant, and, optionally,
(v) 2 mM-80 mM arginine, particularly arginine-HCl.

In another specific embodiment, the present invention provides an aqueous composition having a pH of 5.5-6.5 comprising
(i) an anti-BAFFR antibody wherein the antibody has a concentration of 20 mg/mL-150 mg/mL and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 110 mM-250 mM sucrose or trehalose as a stabilizer,
(iii) 15 mM-25 mM histidine, citrate or succinate as a buffering agent,
(iv) up to 0.02%-0.06% polysorbate 20 or poloxamer 188 or 2 mM-3 mM hydroxyproyl-b-cyclodextrin as a surfactant, and, optionally,
(v) 2 mM-80 mM arginine, particularly arginine-HCl.

In still another specific embodiment, the present invention provides an aqueous composition having a pH of 5.5-6.5 and comprising
(i) an anti-BAFFR antibody wherein the antibody has a concentration of 20 mg/mL-150 mg/mL and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 120 mM-220 mM sucrose or trehalose as a stabilizer,
(iii) 18 mM-22 mM histidine, citrate or succinate as a buffering agent,
(iv) up to 0.02%-0.06% polysorbate 20 or poloxamer 188 or 2.5 mM hydroxyproyl-b-cyclodextrin as a surfactant, and optionally
(v) 2 mM-80 mM arginine, particularly arginine-HCl.

In another specific embodiment, the present invention provides an aqueous composition having a pH of 6.0 and comprising
(i) an anti-BAFFR antibody wherein the antibody has a concentration of 150 mg/mL and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 220 mM sucrose as a stabilizer,
(iii) 20 mM histidine as a buffering agent,
(iv) 0.04% polysorbate 20 as a surfactant.

In another specific embodiment, the present invention provides an aqueous composition having a pH of 6.0 and comprising
(i) an anti-BAFFR antibody wherein the antibody has a concentration of 150 mg/mL and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 220 mM trehalose as a stabilizer,
(iii) 20 mM histidine as a buffering agent,
(iv) 0.04% polysorbate 20 as a surfactant.

In another specific embodiment, the present invention provides an aqueous composition having a pH of 6.0 and comprising
(i) an anti-BAFFR antibody wherein the antibody has a concentration of 150 mg/mL and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 120 mM sucrose or trehalose as a stabilizer,
(iii) 20 mM histidine as a buffering agent,
(iv) 0.04% polysorbate 20 as a surfactant, and
(v) 50 mM arginine, particularly arginine-HCl.

In another specific embodiment, the present invention provides an aqueous composition having a pH of 6.0 and comprising
(i) an anti-BAFFR antibody wherein the antibody has a concentration of 20 mg/mL and wherein said anti-BAFFR antibody includes heavy chain CDR1, CDR2 and CDR3 of SEQ ID NOs 3, 4 and 5 respectively, and light chain CDR1, CDR2 and CDR3 of SEQ ID NOs: 6, 7 and 8,
(ii) 220 mM sucrose or trehalose as a stabilizer,
(iii) 20 mM histidine as a buffering agent, and
(iv) 0.04% polysorbate 20 as a surfactant.

In one embodiment, the invention relates to the aqueous composition of the invention as described herein in the various embodiments, wherein the anti-BAFFR antibody comprises a $V_H$ domain with amino acid SEQ ID NO: 1 and a $V_L$ domain with amino acid SEQ ID NO: 2.

In another embodiment of the invention, the aqueous composition of the invention as described herein in the various embodiments, wherein the anti-BAFFR antibody comprises a heavy chain region of SEQ ID NO: 9 and a light chain region of SEQ ID NO: 10.

In one embodiment, the anti-BAFFR antibody is a non-fucosylated anti-BARR antibody.

The invention further provides a delivery device comprising the aqueous composition of the invention as described herein in the various embodiments.

This delivery device may be provided in form of a pre-filled syringe comprising the aqueous composition of the invention as described herein in the various embodiments.

In one embodiment, the invention relates to a method for delivering an anti-BAFFR antibody to a mammal, comprising the step of administering to said mammal an aqueous composition of the invention as described herein in the various embodiments, particularly in form of a delivery device such as a pre-filled syringe.

The present invention further provides the composition or the delivery device, or the pre-filled syringe of the invention as described herein in the various embodiments, for use in treating a disease or disorder that is mediated by BAFF receptor or that can be treated by killing or depleting B cells.

In particular, the pharmaceutical composition or the delivery device, or the pre-filled syringe of the invention as described herein in the various embodiments may be used in the treatment of autoimmune diseases, B cell neoplasms, such as lymphoma, leukemia or myeloma, rheumatoid arthritis, systemic lupus erythematosus, Sjögren's syndrome or Pemphigus vulgaris.

The invention is based, at least partly, on the properties of formulated antibodies such as MOR6654 and MOR6654B, which retain remarkable stability and bioactive properties when formulated in a high concentration as a liquid (aqueous) composition.

As used herein, an "aqueous" pharmaceutical composition is a composition suitable for pharmaceutical use, wherein the aqueous carrier is distilled water. A composition suitable for pharmaceutical use may be sterile, homogeneous and/or isotonic. Aqueous pharmaceutical compositions may be prepared either directly in an aqueous form, for example in pre-filled syringe ready for use (the "liquid formulations") or as lyophilisate to be reconstituted shortly before use.

As used herein, the term "aqueous pharmaceutical composition" refers to the liquid formulation or reconstituted lyophilized formulation. In certain embodiments, the aqueous pharmaceutical compositions of the invention are suitable for parenteral administration to a human subject. In a specific embodiment, the aqueous pharmaceutical compositions of the invention are suitable for subcutaneous administration.

As used herein, the phrase "parenteral administration" means mode of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The use of antibodies as the active ingredient of pharmaceuticals is now widespread, including the products HERCEPTIN™ (trastuzumab), RITUXAN™ (rituximab), SYNAGIS™ (palivizumab), etc. Techniques for purification of therapeutic antibodies to a pharmaceutical grade are well known in the art.

The composition will usually be non-pyrogenic e.g. containing <1 EU (endotoxin unit, a standard measure) per dose, and preferably <0.1 EU per dose. The composition is preferably gluten-free.

In specific embodiments, the aqueous pharmaceutical compositions of the invention exhibit low to undetectable levels of antibody aggregation or degradation, with very little to no loss of the biological activities during manufacture, preparation, transportation and long periods of storage, the concentration of the anti-BAFFR antibody being at least about 50 mg/mL, 100 mg/mL, 150 mg/mL, 200 mg/mL, 250 mg/mL, or 300 mg/mL.

In one aspect, the invention relates to an aqueous pharmaceutical composition with high concentration of anti-BAFFR antibodies.

It is known in the art that such high concentration aqueous pharmaceutical compositions can be diluted prior to injection, for example, if lower antibody concentrations are required for specific therapeutic interventions or when treating patients of lower body weight including children. Suitable concentrations can be 25 mg/mL or 10 mg/mL. Alternatively, the original formulation may be produced with such a lower concentration.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three or four domains, depending on the isotype, $C_H1$, $C_H2$, $C_H3$ and $C_H4$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of BAFFR). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and $C_H1$ domains; a $F(ab)_2$ fragment, a bivalent fragment comprising two Fab fragments linked by a disulfide bridge at the hinge region; a Fd fragment consisting of the $V_H$ and $C_H1$ domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities, e.g., an isolated antibody that specifically binds human BAFFR is substantially free of antibodies that specifically bind antigens other than BAFFR. An isolated antibody that specifically binds BAFFR may, however, have cross-reactivity to other antigens, such as BAFFR molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86).

The structures and locations of immunoglobulin variable domains, e.g., CDRs, may be defined using well known numbering schemes, e.g., the Kabat numbering scheme, the Chothia numbering scheme, a combination of Kabat and Chothia (AbM), etc. (see, e.g., Sequences of Proteins of Immunological Interest, U.S. Department of Health and Human Services (1991), eds. Kabat et al.; Al Lazikani et al. (1997) J. Mol. Bio. 273:927 948). Throughout this specification, the complementarity determining region ("CDR") is defined according to the Kabat definition with the exception of CDRH1 which is the stretch of amino acids defined by a combination of both Kabat and Chothia definitions for this CDR.

The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgA, IgD, IgE and IgG such as IgG1, IgG2, IgG3 or IgG4) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody that "specifically binds to BAFFR polypeptide" or an "anti-BAFFR antibody" refers to an antibody that binds to human BAFFR polypeptide of SEQ ID NO: 13 with a $K_D$ of 100 nM or less, 10 nM or less, 1 nM or less. An antibody that "cross-reacts with an antigen other than BAFFR" refers to an antibody that binds that antigen with a $K_D$ of $0.5 \times 10^{-8}$ M or less, $5 \times 10^{-9}$ M or less, or $2 \times 10^{-9}$ M or less. An antibody that "does not cross-react with a particular antigen" is intended to refer to an antibody that binds to that antigen, with a $K_D$ of $1.5 \times 10^{-8}$ M or greater, or a $K_D$ of $5-10 \times 10^{-8}$ M or $1 \times 10^{-7}$ M or greater. In certain embodiments, such antibodies that do not cross-react with the antigen exhibit essentially undetectable binding against these proteins in standard binding assays.

In one embodiment, a high concentration of an anti-BAFFR antibody in the aqueous pharmaceutical composition of the invention is at least 50 mg/mL. In one embodiment, a high concentration is at least 100 mg/mL. In one embodiment, a high concentration is at least 150 mg/mL. In one embodiment, a high concentration is at least 200 mg/mL. In one embodiment, a high concentration is at least 250 mg/mL. In one embodiment, a high concentration is at least 270 mg/mL. In one embodiment, a high concentration is at least 300 mg/mL.

In one embodiment, the aqueous pharmaceutical composition of the invention comprises between 50 mg/mL and 300 mg/mL of an anti-BAFFR antibody, for example, MOR6654, especially MOR6654B.

In one embodiment, the aqueous pharmaceutical composition of the invention comprises between 75 mg/mL and 270 mg/mL of an anti-BAFFR antibody, for example, MOR6654, especially MOR6654B.

In one embodiment, the aqueous pharmaceutical composition of the invention comprises between 100 mg/mL and 250 mg/mL of an anti-BAFFR antibody, for example, MOR6654, especially MOR6654B.

In one embodiment, the aqueous pharmaceutical composition of the invention comprises between 100 mg/mL and 200 mg/mL of an anti-BAFFR antibody, for example, MOR6654, especially MOR6654B.

In one embodiment, the aqueous pharmaceutical composition of the invention comprises 150 mg/mL of an anti-BAFFR antibody, for example, MOR6654, especially MOR6654B.

In one embodiment, the aqueous pharmaceutical composition of the invention comprises 20 mg/mL of an anti-BAFFR antibody, for example, MOR6654, especially MOR6654B.

In one embodiment, the aqueous pharmaceutical composition of the invention comprises about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 270 mg/mL or about 300 mg/mL of an anti-BAFFR antibody, for example, MOR6654, especially MOR6654B.

Furthermore, the aqueous pharmaceutical compositions according to the invention as described herein in the various embodiments are stable such that, even after storage for 4 weeks at 2-8° C., less than 5%, 4%, 3%, 2%, 1%, 0.05% or 0.01% of the total anti-BAFFR antibody is aggregated as measured by SEC-HPLC.

The aqueous pharmaceutical compositions according to the invention as described herein in the various embodiments are stable such that, even after storage for 2 month at 2-8° C., less than 5%, 4%, 3%, 2%, 1%, 0.05% or 0.01% of the total anti-BAFFR antibody is aggregated as measured by SEC-HPLC.

The aqueous pharmaceutical compositions may include, in addition to the anti-BAFFR antibody, further components such as one or more of the following: (i) a stabilizer; (ii) a buffering agent; (iii) a surfactant; and (iv) a free amino acid. Inclusion of each of such additional components can give compositions with low aggregation of the anti-BAFFR antibody.

Suitable stabilizer for use with the invention can act, e.g., as viscosity enhancing agents, bulking agents, solubilizing agents, and/or the like. The stabilizer can be ionic or non ionic (e.g. sugars). As sugars they include, but are not limited to, monosaccharides, e.g., fructose, maltose, galactose, glucose, D-mannose, sorbose and the like; disaccharides, e.g. lactose, sucrose, trehalose, cellobiose, and the like; polysaccharides, e.g. raffinose, melezitose, maltodextrins, dextrans, starches, and the like; and alditols, such as mannitol, xylitol, maltitol, lactitol, xylitol sorbitol (glucitol) and the like. For example, the sugar may be sucrose, trehalose, raffinose, maltose, sorbitol or mannitol. The sugar may be a sugar alcohol or an amino sugar. Sucrose is particularly useful. As ionic stabilizer they include salts such as NaCl or amino acid components such as arginine-HCl.

Suitable buffering agents for use with the invention include, but are not limited to, organic acid salts such as salts of citric acid, ascorbic acid, gluconic acid, carbonic acid, tartaric acid, succinic acid, acetic acid or phtalic acid; Tris, thomethamine hydrochloride, or phosphate buffer. In addition, amino acid components can also be used as buffering agent. Such amino acid component includes without limitation glycine and histidine. A histidine buffer is particularly useful.

The aqueous pharmaceutical compositions include such buffering agent or pH adjusting agent to provide improved pH control. In one embodiment, an aqueous pharmaceutical composition of the invention has a pH between 5.0 and 8.0, between 5.0 and 7.0, between 5.5 and 7.0, or between 5.5 and 6.5. In a specific embodiment, an aqueous pharmaceutical composition of the invention has a pH of about 6.0.

As used herein, the term "surfactant" refers to organic substances having amphipathic structures; i.e., they are composed of groups of opposing solubility tendencies, typically an oil-soluble hydrocarbon chain and a water-soluble ionic group. Surfactants can be classified, depending on the charge of the surface-active moiety, into anionic, cationic and dispersing agents for various pharmaceutical compositions and preparations of biological materials.

Suitable surfactants for use with the invention include, but are not limited to, non-ionic surfactants, ionic surfactants and zwitterionic surfactants. Typical surfactants for use with the invention include, but are not limited to, sorbitan fatty acid esters (e.g. sorbitan monocaprylate, sorbitan monolaurate, sorbitan monopalmitate), sorbitan trioleate, glycerine fatty acid esters (e.g. glycerine monocaprylate, glycerine monomyristate, glycerine monostearate), polyglycerine fatty acid esters (e.g. decaglyceryl monostearate, decaglyceryl distearate, decaglyceryl monolinoleate), polyoxyethylene sorbitan fatty acid esters (e.g. polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g. polyoxyethylene sorbitol tetrastearate, polyoxyethylene sorbitol tetraoleate), polyoxyethylene glycerine fatty acid esters (e.g. polyoxyethylene glyceryl monostearate), polyethylene glycol fatty acid esters (e.g. polyethylene glycol distearate), polyoxyethylene alkyl ethers (e.g. polyoxyethylene lauryl ether), polyoxyethylene polyoxypropylene alkyl ethers (e.g. polyoxyethylene polyoxypropylene glycol, polyoxyethylene polyoxypropylene propyl ether, polyoxyethylene polyoxypropylene cetyl ether), polyoxyethylene alkylphenyl ethers (e.g. polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g. polyoxyethylene sorbitol beeswax), polyoxyethylene lanolin derivatives (e.g. polyoxyethylene lanolin), and polyoxyethylene fatty acid amides (e.g. polyoxyethylene stearic acid amide); $C_{10}$-$C_{18}$ alkyl sulfates (e.g. sodium cetyl sulfate, sodium lauryl sulfate, sodium oleyl sulfate), polyoxyethylene $C_{10}$-$C_{18}$ alkyl ether sulfate with an average of 2 to 4 moles of ethylene oxide units added (e.g. sodium polyoxyethylene lauryl sulfate), and $C_1$-$C_{18}$ alkyl sulfosuccinate ester salts (e.g. sodium lauryl sulfosuccinate ester); and natural surfactants such as lecithin, glycerophospholipid, sphingophospholipids (e.g. sphingomyelin), and sucrose esters of $C_{12}$-$C_{18}$ fatty acids. A composition may include one or more of these surfactants. Preferred surfactants are polyoxyethylene sorbitan fatty acid esters e.g. polysorbate 20, 40, 60 or 80. Polysorbate 20 (Tween 20) is particularly useful.

Suitable free amino acids for use with the invention include, but are not limited to, arginine, lysine, histidine, ornithine, isoleucine, leucine, alanine, glycine glutamic acid or aspartic acid. The inclusion of a basic amino acid is preferred i.e. arginine, lysine and/or histidine. If a composition includes histidine then this may act both as a buffering agent and a free amino acid, but when a histidine buffer is used it is typical to include a non-histidine free amino acid e.g. to include histidine buffer and lysine. An amino acid may be present in its D- and/or L-form, but the L-form is typical. The amino acid may be present as any suitable salt e.g. a hydrochloride salt, such as arginine-HCl.

Other contemplated excipients, which may be utilized in the aqueous pharmaceutical compositions of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, 4th edition, Rowe et al., Eds., American Pharmaceuticals Association (2003); and Remington: the Science and Practice of Pharmacy, 21th edition, Gennaro, Ed., Lippincott Williams & Wilkins (2005).

The aqueous pharmaceutical compositions of the invention may include further active ingredients in addition to the anti-BAFFR antibody. Further pharmacological agents may include, for instance, chemotherapeutic compounds.

Target Diseases and Disorders

The aqueous pharmaceutical compositions of the invention comprising anti-BAFFR antibodies can be used to treat, ameliorate or prevent a variety of diseases or disorders. Pharmaceutical compositions comprising anti-BAFFR antibodies are particularly useful to treat BAFFR related disorders such as autoimmune disorders, e.g., systemic lupus erythematosus, Sjögren's syndrome, Pemphigus vulgaris, rheumatoid arthritis, multiple sclerosis and B cell neoplasms such as acute lymphoblastic leukemia (ALL) and B-cell chronic lymphocytic leukemia (CLL).

As used herein, "a BAFFR-related disorder" includes conditions associated with or characterized by aberrant BLyS levels and/or diseases or conditions that can be treated by depleting or killing B cells. These includes, without limitations, inflammatory conditions, autoimmune diseases, severe infections, and organ or tissue transplant rejection. These further include B-cell neoplasms.

For example, the aqueous pharmaceutical compositions of the invention comprising anti-BAFFR antibodies may be used for the treatment, amelioration or prevention of recipients of heart, lung, combined heart-lung, liver, kidney, pancreatic, skin or conical transplants, including allograft rejection or xenograft rejection, and for the prevention of graft-versus-host disease, such as following bone marrow transplant, and organ transplant associated arteriosclerosis. Further, the aqueous pharmaceutical compositions of the invention are useful in solid organ transplantation and in antibody-mediated acute and chronic transplant rejection.

The aqueous pharmaceutical compositions of the invention comprising anti-BAFFR antibodies are useful for the treatment, prevention, or amelioration of autoimmune disease and of inflammatory conditions, in particular inflammatory conditions with an etiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankylosing spondylitis, Reiter syndrome, reactive arthritis, psoriatic arthritis, and enterophathics arthritis, hypersensitivity (including both airways hypersensitivity and dermal hypersensitivity) and allergies. Specific auto-immune diseases for which antibodies of the invention may be employed include autoimmune haematological disorders (including e.g. hemolytic anaemia, aplastic anaemia, pure red cell anaemia and idiopathic thrombocytopenia), acquired hemophilia A, cold agglutinin disease, cryoglobulinemia, thrombotic thrombocytopenic purpura, Sjögren's syndrome, systemic lupus erythematosus, inflammatory muscle disorders, polychondritis, scleroderma, vasculitis such as cryoglobulinemia, large vessel vasculitides such as giant cell arteritis, polymyalgia rheumatica, necrotizing vasculitides, including anti-neutrophil cytoplasmic antibody-associated vasculitis, Takayasu's arteritis, polyarteritis nodosa, Henoch-Schonlein purpura, and Churg-Strauss syndrome, IgM mediated neuropathy, seronegative spondarthritis, opsoclonus myoclonus syndrome, Wegener granulomatosis, dermatomyositis, anti-neutrophil cytoplasmatic autoantibody (ANCA) vasculitis, chronic active hepatitis, myasthenia gravis, psoriasis, Steven-Johnson syndrome, pemphigus vulgaris, pemphigus foliacius, idiopathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, neuromyelitis optica, primary biliary cirrhosis, juvenile diabetes (diabetes mellitus type I), uveitis (anterior, intermediate and posterior as well as panuveitis), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), acute nephritic lupus, tumors, inflammatory disease of skin and cornea, myositis, loosening of bone implants, metabolic disorders, such as atherosclerosis, diabetes, and dislipidemia.

The aqueous pharmaceutical compositions of the invention may also be useful in preventing, ameliorating or treating B-cell neoplasms. Examples of such diseases and conditions include, but are not limited to, B-cell Non-Hodgkin's lymphomas, such as small lymphocytic lymphoma, lymphoplasmacytoid lymphoma, mantle cell lymphoma, follicular lymphoma, mucosa-associated lymphoid tissue lymphoma, diffuse large cell lymphoma, and Burkitt's lymphoma; acute lymphoblastic leukemia (ALL), precursor B-lymphoblastic leukemia; B-cell chronic lymphocytic leukemia (CLL), and multiple myeloma. Other B-cell neoplasms are encompassed within the scope of the invention.

Patient Administration

A pharmaceutical composition of the invention can be administered to a patient. Administration will typically be by infusion or via a syringe. Thus, the invention provides a delivery device (e.g. a syringe) including a pharmaceutical composition of the invention (e.g., pre-filled syringe). Patients will receive an effective amount of the anti-BAFFR antibody as the principal active ingredient i.e. an amount that is sufficient to treat, ameliorate, or prevent the disease or disorder in question. Therapeutic effects may also include reduction in physical symptoms. The optimum effective amount and concentration of antibody for any particular subject will depend upon various factors, including the patient's age size health and/or gender, the nature and extent of the condition, the activity of the particular antibody, the rate of its clearance by the body, and also on any possible further therapeutic(s) administered in combination with the antibody. The effective amount delivered for a given situation can be determined within the judgment of a clinician. For purposes of the present invention, an effective dose may be from about 0.005 mg/kg to about 50 mg/kg, or about 0.05 mg/kg to about 10 mg/kg. Known antibody-based pharmaceuticals provide guidance in this respect e.g. HERCEPTIN™ is administered with an initial loading dose of 4 mg/kg body weight and a weekly maintenance dose of 2 mg/kg body weight; RITUXAN™ is administered weekly at 375 mg/m$^2$; SYNAGIS™ is administered intramuscularly at 15 mg/kg body weight; etc.

The invention provides a method for delivering a monoclonal antibody to a mammal, comprising a step of administering to the patient a pharmaceutical composition of the invention.

The invention also provides formulations of the invention as described herein in the various embodiments for use as medicaments e.g. for use in delivering an antibody to a mammal, or for use in treating, preventing or ameliorating one or more of the diseases and disorders described above.

The mammal is preferably a human but may also be, for example, a horse or a cow or a dog or a cat. The antibodies will ideally be chosen to match the target species e.g. a human antibody for human administration, an equine antibody for horses, a canine antibody for dogs, etc. If native host antibodies are not available then transfer of antibody specificity from one species to another can be achieved by transfer of CDR residues (and typically, in addition, one or more framework residues) from a donor antibody into a recipient framework from the host species e.g. as in humanization. Equinized, bovinized, caninized and felinized antibodies are known in the art. The antibody will bind to BAFFR from the target species, but it may also cross-react with BAFFR from other species.

Dosage can be by a single dose schedule or a multiple dose schedule.

Ingredients for forming compositions of the invention may be supplied in hermetically-sealed containers.

The Anti-BAFFR Antibody

The invention concerns the formulation of anti-BAFFR antibodies and more specifically MOR6654 and MOR6654B.

One suitable antibody that can be comprised in the pharmaceutical compositions of the invention is the human recombinant antibody MOR6654, structurally characterized as further described below. The $V_H$ amino acid sequence of such isolated anti-BAFFR antibody is shown in SEQ ID NO: 1. The $V_L$ amino acid sequence of such isolated anti-BAFFR antibody is shown in SEQ ID NO: 2. An example of the full length heavy chain amino acid sequence of such isolated anti-BAFFR antibody is shown in SEQ ID NO: 9. An example of the full-length light chain amino acid sequence of such isolated anti-BAFFR antibody is shown in SEQ ID NO: 10. Another example of heavy and light chain amino acid sequences of such isolated anti-BAFFR antibodies are those encoded by the nucleotide sequences of SEQ ID NO: 11 and SEQ ID NO: 12 respectively. Another example of heavy and light chain amino acid sequences of antibodies are those encoded by corresponding DNA sequences contained in plasmid pBW510 as deposited by Novartis Pharma AG, Forum 1, CH-4002 Basel, Switzerland, at DSMZ, Inhoffenstrasse 7B, 38124 Braunschweig, Germany on Apr. 29, 2009 with accession number DSM22542.

Other anti-BAFFR antibodies that can be used for preparing the pharmaceutical compositions of the invention include anti-BAFFR antibodies, with amino acids that have been mutated by amino acid deletion, insertion or substitution, yet have no more than 1, 2, 3, 4 or 5 amino acid deletion, insertion or substitution in either the heavy or light chain regions described above. In a specific embodiment, such amino acid changes appear only within the framework and/or constant regions and the CDR regions are 100% identical to the heavy chain CDR1, CDR2 and CDR3 regions of SEQ ID NO: 3, 4 and 5 and to the light chain CDR1, CDR2 and CDR3 regions of SEQ ID NO: 6, 7, and 8 respectively. In one more specific embodiment, the changes that have been made are only conservative amino acid substitutions outside of the CDR regions.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues outside of the CDR regions of an anti-BAFFR antibody, can be replaced with other amino acid residues from the same side chain family, and the altered antibody can be tested for retained function, in particular the same binding properties to BAFFR.

Antibodies may typically be glycosylated. N-linked glycans attached to the $C_H2$ domain of a heavy chain, for instance, can influence C1q and FcR binding, and aglycosylated antibodies may have lower or different affinity for these receptors. The glycan structure can also affect activity e.g. differences in complement-mediated cell death may be seen depending on the number of galactose sugars (0, 1 or 2) at the terminus of a glycan's biantennary chain. An antibody's glycans preferably do not lead to a human immunogenic response after administration.

Additionally or alternatively, an antibody can be made that has an altered type of glycosylation, such as a hypofucosylated or non-fucosylated antibody having reduced amounts of or no fucosyl residues or an antibody having increased bisecting GleNac structures. Such altered glycosylation patterns have been demonstrated to increase the antibody-dependent cell-mediated cytotoxicity (ADCC) ability of antibodies. Such carbohydrate modifications can be accomplished by, for example, expressing the antibody in a host cell with altered glycosylation machinery. Cells with an altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the anti-BAFFR antibodies that are included in the pharmaceutical compositions of the invention are produced by recombinant expression in a cell line which exhibit hypofucosylation or non-fucosylation pattern, for example, a mammalian cell line with deficient expression of the FUT8 gene encoding fucosyltransferase.

As used herein, the term MOR6654 encompasses any type of glycosyation pattern. In a specific embodiment, the pharmaceutical compositions comprises an anti-BAFFR antibody consisting of MOR6654 as produced in a cell line which exhibits a hypofucosylation or non-fucosylation pattern, such as MOR6654B, which exhibit non-fucosylation pattern (devoid of fucosyl residues). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues. Alternatively, the anti-BAFFR antibodies can be produced in yeasts or filamentous fungi engineered for mammalian-like glycosylation pattern and capable of producing antibodies lacking fucose as glycosylation pattern (see for example EP1297172B1).

Another modification of the anti-BAFFR antibodies herein that is contemplated by the invention is pegylation. An antibody can be pegylated to, for example, increase the biological (e.g., serum) half-life of the antibody. To pegylate an antibody, the antibody, or fragment thereof, typically may be reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer).

As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Any other natural or non-natural post-translational modification of anti-BAFFR antibodies (e.g. MOR6654) is further contemplated as specific embodiments of anti-BAFFR antibodies that could be used for preparing the pharmaceutical compositions of the invention.

Antibodies can be prepared in a form free from products with which they would naturally be associated. Contaminant components of an antibody's natural environment include materials such as enzymes, hormones, or other host cell proteins.

EXAMPLES

Preparing Anti-BAFFR Antibodies

Antibody MOR6654 binds specifically to BAFFR and is also described in international application published as WO2010/007082. It is a human IgG1 kappa antibody obtained via phage display. Its heavy and light chains consist of SEQ ID NOs: 9 and 10. The Tables 1 and 2 below summarize the sequence characteristics of MOR6654.

TABLE 1

Brief description of the sequences listed in the sequence listing of Table 2

| SEQ ID NO: | Description of the sequence |
|---|---|
| 1 | Amino acid sequence of the variable region ($V_H$) of the heavy chain of MOR6654 |
| 2 | Amino acid sequence of the variable region ($V_L$) of the light chain of MOR6654 |
| 3 | Amino acid sequence of HCDR1 of MOR6654 |
| 4 | Amino acid sequence of HCDR2 of MOR6654 |
| 5 | Amino acid sequence of HCDR3 of MOR6654 |
| 6 | Amino acid sequence of LCDR1 of MOR6654 |
| 7 | Amino acid sequence of LCDR2 of MOR6654 |
| 8 | Amino acid sequence of LCDR3 of MOR6654 |
| 9 | Amino acid sequence of the full length heavy chain of MOR6654 |
| 10 | Amino acid sequence of the full length light chain of MOR6654 |
| 11 | Nucleotide sequence encoding SEQ ID NO: 1 |
| 12 | Nucleotide sequence encoding SEQ ID NO: 2 |
| 13 | Human BAFFR amino acid sequence |
| 14 | Full length nucleotide sequence (including leader sequence and constant part) of MOR6654 heavy chain; nt 1-57 = leader; nt 58-429 = VH; nt 430-1419 = constant region (hIgG1) |
| 15 | Full length nucleotide sequence (including leader sequence and constant part) of MOR6654 light chain; nt 1-60 = leader; nt 61-384 = VL; nt 385-705 = constant region (hkappa) |

TABLE 2

Sequence listing

| SEQ ID NO: | Amino acid or Nucleotide Sequence |
|---|---|
| 1 | QVQLQQSGPGLVKPSQTLSLTCAISGDSVSSNSAAWGWIRQSPGRGLEWLGRIYYRSKWYNSYAVSVKSRITINPDTSKNQFSLQLNSVTPEDTAVYYCARYDWVPKIGVFDSWGQGTLVTVSS |
| 2 | DIVLTQSPATLSLSPGERATLSCRASQFISSSYLSWYQQKPGQAPRLLIYGSSSRATGVPARFSGSGSGTDFTLTISSLEPEDFAVYYCQQLYSSPMTFGQGTKVEIK |
| 3 | GDSVSSNSAAWG |
| 4 | RIYYRSKWYNSYAVSVKS |
| 5 | YDWVPKIGVFDS |
| 6 | RASQFISSSYLS |
| 7 | GSSSRAT |
| 8 | QQLYSSPMT |
| 9 | QVQLQQSGPGLVKPSQTLSLTCAISGDSVSSNSAAWGWIRQSPGRGLEWLGRIYYRSKWYNSYAVSVKSRITINPDTSKNQFSLQLNSVTPEDTAVYYCARYDWVPKIGVFDSWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 10 | DIVLTQSPATLSLSPGERATLSCRASQFISSSYLSWYQQKPGQAPRLLIYGSSSRATGVPARFSGSGSGTDFTLTISSLEPEDFAVYYCQQLYSSPMTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 11 | CAGGTGCAGCTGCAGCAGAGCGGCCCAGGCCTGGTCAAGCCCTCTCAGACCCTGTCACTGACCTGCGCCATTTCAGGCGACAGCGTGAGCAGCAACAGCGCCGCCTGGGGCTGGATCAGGCAGAGCCCCGGTAGGGGCCTGGAATGGCTGGGCAGGATCTACTACAGGTCCAAGTGGTACAACAGCTACGCCGTGAGCGTGAAGAGCAGGATCACCATCAACCCTGACACCAGCAAGAACCAGTT |

TABLE 2-continued

Sequence listing

| SEQ ID NO: | Amino acid or Nucleotide Sequence |
|---|---|
|  | CTCACTGCAGCTCAACAGCGTGACCCCCGAGGACACCGCCGTGTACTAC<br>TGCGCCAGATACGACTGGGTGCCCAAGATCGGCGTGTTCGACAGCTGGG<br>GCCAGGGCACCCTGGTGACCGTGTCAAGC |
| 12 | GATATCGTGCTGACACAGAGCCCCGCCACCCTGAGCCTGAGCCCAGGCG<br>AGAGGGCCACCCTGTCCTGCAGGGCCAGCCAGTTTATCAGCAGCAGCTA<br>CCTGTCCTGGTATCAGCAGAAGCCCGGCCAGGCCCCTAGACTGCTGATC<br>TACGGCAGCTCCTCTCGGGCCACCGGCGTGCCCGCCAGGTTCAGCGGC<br>AGCGGCTCCGGCACCGACTTCACCCTGACAATCAGCAGCCTGGAGCCCG<br>AGGACTTCGCCGTGTACTACTGCCAGCAGCTGTACAGCTCACCCATGACC<br>TTCGGCCAGGGCACCAAGGTGGAGATCAAG |
| 13 | MRRGPRSLRGRDAPAPTPCVPAECFDLLVRHCVACGLLRTPRPKPAGASSP<br>APRTALQPQESVGAGAGEAALPLPGLLFGAPALLGLALVLALVLVGLVSWRR<br>RQRRLRGASSAEAPDGDKDAPEPLDKVIILSPGISDATAPAWPPPGEDPGTT<br>PPGHSVPVPATELGSTELVTTKTAGPEQQ |
| 14 | ATGGCCTGGGTGTGGACCCTGCCCTTCCTGATGGCCGCTGCCCAGTCAG<br>TGCAGGCCCAGGTGCAGCTGCAGCAGAGCGGCCCAGGCCTGGTCAAGC<br>CCTCTCAGACCCTGTCACTGACCTGCGCCATTTCAGGCGACAGCGTGAG<br>CAGCAACAGCGCCGCCTGGGGCTGGATCAGGCAGAGCCCCGGTAGGGG<br>CCTGGAATGGCTGGGCAGGATCTACTACAGGTCCAAGTGGTACAACAGCT<br>ACGCCGTGAGCGTGAAGAGCAGGATCACCATCAACCCTGACACCAGCAA<br>GAACCAGTTCTCACTGCAGCTCAACAGCGTGACCCCCGAGGACACCGCC<br>GTGTACTACTGCGCCAGATACGACTGGGTGCCCAAGATCGGCGTGTTCG<br>ACAGCTGGGGCCAGGGCACCCTGGTGACCGTGTCAAGCGCCAGCACCAA<br>GGGCCCCAGCGTGTTCCCCCTGGCCCCCAGCAGCAAGAGCACCAGCGG<br>CGGCACAGCCGCCCTGGGCTGCCTGGTGAAGGACTACTTCCCCGAGCCC<br>GTGACCGTGTCCTGGAACAGCGGAGCCCTGACCTCCGGCGTGCACACCT<br>TCCCCGCCGTGCTGCAGAGCAGCGGCCTGTACAGCCTGTCCAGCGTGGT<br>GACAGTGCCCAGCAGCAGCCTGGGCACCCAGACCTACATCTGCAACGTG<br>AACCACAAGCCCAGCAACACCAAGGTGGACAAGAGAGTGGAGCCCAAGA<br>GCTGCGACAAGACCCACACCTGCCCCCCCTGCCCAGCCCCAGAGCTGCT<br>GGGCGGACCCTCCGTGTTCCTGTTCCCCCCCAAGCCCAAGGACACCCTG<br>ATGATCAGCAGGACCCCCGAGGTGACCTGCGTGGTGGTGGACGTGAGCC<br>ACGAGGACCCAGAGGTGAAGTTCAACTGGTACGTGGACGGCGTGGAGGT<br>GCACAACGCCAAGACCAAGCCCAGAGAGGAGCAGTACAACAGCACCTAC<br>AGGGTGGTGTCCGTGCTGACCGTGCTGCACCAGGACTGGCTGAACGGCA<br>AGGAATACAAGTGCAAGGTCTCCAACAAGGCCCTGCCAGCCCCCATCGA<br>AAAGACCATCAGCAAGGCCAAGGGCCAGCCACGGGAGCCCCAGGTGTAC<br>ACCCTGCCCCCCTCCCGGGAGGAGATGACCAAGAACCAGGTGTCCCTGA<br>CCTGTCTGGTGAAGGGCTTCTACCCCAGCGACATCGCCGTGGAGTGGGA<br>GAGCAACGGCCAGCCCGAGAACAACTACAAGACCACCCCCCCAGTGCTG<br>GACAGCGACGGCAGCTTCTTCCTGTACAGCAAGCTGACCGTGGACAAGT<br>CCAGGTGGCAGCAGGGCAACGTGTTCAGCTGCAGCGTGATGCACGAGGC<br>CCTGCACAACCACTACACCCAGAAGAGCCTGAGCCTGTCCCCCGGCAAG |
| 15 | ATGAGCGTGCTGACCCAGGTGCTGGCTCTGCTGCTGCTGTGGCTGACCG<br>GCACCAGATGCGATATCGTGCTGACACAGAGCCCCGCCACCCTGAGCCT<br>GAGCCCAGGCGAGAGGGCCACCCTGTCCTGCAGGGCCAGCCAGTTTATC<br>AGCAGCAGCTACCTGTCCTGGTATCAGCAGAAGCCCGGCCAGGCCCCTA<br>GACTGCTGATCTACGGCAGCTCCTCTCGGGCCACCGGCGTGCCCGCCAG<br>GTTCAGCGGCAGCGGCTCCGGCACCGACTTCACCCTGACAATCAGCAGC<br>CTGGAGCCCGAGGACTTCGCCGTGTACTACTGCCAGCAGCTGTACAGCT<br>CACCCATGACCTTCGGCCAGGGCACCAAGGTGGAGATCAAGCGTACGGT<br>GGCCGCTCCCAGCGTGTTCATCTTCCCCCCCAGCGACGAGCAGCTGAAG<br>AGCGGCACCGCCAGCGTGGTGTGCCTGCTGAACAACTTCTACCCCCGGG<br>AGGCCAAGGTGCAGTGGAAGGTGGACAACGCCCTGCAGAGCGGCAACA<br>GCCAGGAGAGCGTCACCGAGCAGGACAGCAAGGACTCCACCTACAGCCT<br>GAGCAGCACCCTGACCCTGAGCAAGGCCGACTACGAGAAGCATAAGGTG<br>TACGCCTGCGAGGTGACCCACCAGGGCCTGTCCAGCCCCGTGACCAAGA<br>GCTTCAACAGGGGCGAGTGC |

Examples of Formulations

A high concentration liquid formulation of MOR6654B was desired and so formulation studies were performed. A liquid formulation comprising a sugar, a buffering agent and a surfactant was stable and could maintain high antibody concentrations.

The antibody may be produced in mammalian host cells, such as, a CHO cell line transfected with expression vectors carrying heavy and light chain coding sequences under suitable expression promoters.

The antibody is preferably produced in a mammalian cell line, e.g. a CHO cell line, modified by using, for example, the Potelligent™ technology (BioWa, Inc.) leading to deficient expression of the FUT8 gene encoding fucosyltransferase. The resulting antibody is non-fucosylated and designated herein as MOR6654B.

The development of a liquid MOR6654B formulation in a vial or a pre-filled syringe consisted of two studies. A first screen was made to define the excipients in the formulation. In a second screen the selected formulation was confirmed in the final primary packaging.

Stability and Analytical Plan

The following analytical methods were performed: UV Assay, Size Exclusion Chromatography HPLC, Dynamic Light Scattering, Cationic Exchange Chromatography HPLC, Reverse Phase Chromatography HPLC, ALP Analyzer, Turbidity, pH value, osmolality, MFI (Micro-Flow Imaging), viscosity, color, visual inspection.

Stability Determination

Stability was further determined after subjecting the formulations to certain stress conditions including agitation, freeze-thaw cycles and prolonged exposure to light (1 month at 40° C.).

Turbidimetric Method

Turbidity was measured by a turbidimetric method.

The turbidimeter measurements for the samples were performed by following the operational manual (Model 2100AN Instrument Manual, Number: 47901-88, November 2006, Edition 2). At the start of the analysis the calibration curve for the instrument was checked by analyzing 5 calibration samples, including water. If the values measured by the instrument were within 5% of the standards value, than the calibration curve passed. If any of the standards failed the 5% acceptance criteria, than the instrument was recalibrated following the operational manual. After the instrument passed calibration, the samples were loaded in 11 mm flat bottom text tubes and analyzed.

Size Exclusion Chromatographic (SEC) Method

In the SEC method used to analyze the liquid formulations, the following method parameters were used:
Column: TSKgel G3000SWXL
Analysis Buffer: 150 mM K-phosphate, pH 6.5+/−0.1
Flow Rate: 0.4 mL/min
Column temperature: 30° C.
Detection: 210 nm
Injection volume: 10 ul
Sample temperature: approx. 5° C.
Run time: 40 minutes
Data sampling rate: 1.0 points/second (Chromeleon step=1.0)

Cation Exchange Chromatography (CEX) HPLC Method

The first step for sample analysis using the CEX HPLC method was to dilute all formulations to 10 mg/mL using water. The second step was taking the 10 mg/mL diluted sample and diluting again with mobile phase A to 3 mg/mL. The sample was then loaded into the HPLC and analyzed.
Mobile Phase A: 25 mM sodium phosphate, pH 6.5
Mobile Phase B: 25 mM sodium phosphate, 250 mM NaCl, pH 6.5
Flow Rate: 1.0 mL/min
Column Temperature: 30° C.+/−2° C.
Sample Temperature: 5° C.+/−2° C.
Injection Volume: 40 ul
Run Time (min): 60
Detection: 215 nm
Gradient:

| Time | % A | % B |
|------|-----|-----|
| 0    | 100 | 0   |
| 46   | 0   | 100 |
| 51   | 0   | 10  |
| 52   | 100 | 0   |
| 60   | 100 | 0   |

RP HPLC Method

The RP HPLC method used to analyze the LB-120 samples was performed by following the following RP method parameters. The gradient in the testing protocol resulted in the protein being eluded in the column void volume.
Method Parameters
Column Information: PoroShell 300SB-C8
Mobile Phase A: 90% (v/v) H2O/10% (v/v) ACN/0.1% (v/v) TFA
Mobile Phase B: 10% (v/v) H2O/90% (v/v) ACN/0.1% (v/v) TFA
Flow rate: 2 mL/min
Column temperature: 80° C.
Detection: 210 nm
Injection volume: 5 µL
Sample temperature: Approx. 5° C.
Run time: 6 minutes
Gradient:

| Time | % A | % B |
|------|-----|-----|
| 0    | 90  | 10  |
| 5    | 75  | 25  |
| 5.1  | 90  | 10  |
| 6    | 90  | 10  |

MFI Method

All of the stability samples were tested using a Protein Simple Micro-Flow Imaging (MFI) instrument, model DPA 4200 with a standard 100 µm flow cell (1.6 mm, SP3 with Silane coating, cat#4002-002-001) and a 5× objective. The software version for MFI View System Software was 2-R2.6.2.21.2171.

The instrument set-up and selected features included:
Edge Particle Rejection—selected
Fill Particles—selected (except T0)
Sample Volume: 0.5 mL
Purge Volume: 0.15 mL
Approximate Sample Volume: 0.30 mL (auto calculated)

On the day of testing, either three (single testing) or four (duplicate testing) syringes per each condition were pooled into individual 15 mL Nunc tubes (Catalogue#339651). All work was performed in a laminar flow hood and MFI samples were tested undiluted.

Run sequences consisted of running water blanks prior to each sample and standard to ensure background levels of particles were with reason (typically below 600 particles/mL or less than 1% of sample particles/mL). Water flushes of 30 mL or more were used between different samples and between samples and standards prior to measuring background particle levels (blanks). If blanks were not acceptable additional flushing was performed and another blank was run. Water flushes of 10 mL were used between replicate samples and replicate standards to adequately clear the system of air bubbles and reduce particles. Millipore Direct-Q type 1 water was used for blanks and flushing (0.22 µm filtered, 18.2 MΩ quality). Neptune Barrier 1000 µl Tips used to deliver sample to the sample inlet port.

Each sample sequence contained a number of NIST (National Institute of Standard and Technology) certified 5.0 μm particle standards containing 3000 particles/mL greater than or equal to 3 μm in size (Cat# CC05, Lot 39588, Exp. July 2012) to determine reproducibility during the run. The performance of the standards is listed in Table 3.

TABLE 3

Analysis summary of NIST particle standards using MFI

| Time point | Blank Average | Std Average | 3 Std Deviations | # of Stds | Lot# |
|---|---|---|---|---|---|
| T0 | 207 | 3105 | ±16% | 4 | 39588, bottle 2 |
| T1 | 304 | 2222 | ±6% | 4 | 39588, bottle 2 |
| T2 | 337 | 3109 | ±16% | 7 | 39588, 042512 |

Individual particle size was determined by using Protein Simples measurement technique known as Equivalent Circular Diameter (ECD). The ECD of an object is expressed in microns and represents the diameter of a sphere that occupies the same two-dimensional surface area as the particle. The MFI product platform converts the area of an object into an ECD value using proprietary conversion techniques to avoid the error inherent with performing direct calculations based on field of view dimensions. The conversion techniques are based on a mapping of the entire instrument size range using NIST traceable polystyrene beads. Although the conversion is based on polystyrene beads, the vendors claim is that the unique operation of the MFI product platform will guarantee the results obtained from the instrument are insensitive to the particle material properties. Therefore, the instrument does not require calibration against specific sample types for proper operation.

Colorimetric Method

Sample color was analyzed using a standard testing procedure. The color value for each sample is recorded in the European Pharmacopoeia (EP) color definition (Table 4). An example, B1 to B9 is the brown color scale as defined in the European Pharmacopoeia.

TABLE 4

Color Range for the European Pharmacopoeia

| From | To | Description |
|---|---|---|
| Y7 | Y1 | Yellow Color Scale |
| B9 | B1 | Brown Color Scale |
| BY7 | BY1 | Brown-Yellow Color Scale |
| GY7 | GY1 | Green-Yellow Color Scale |
| R7 | R1 | Red Color Scale |

Photostability Testing

Syringes containing each of the four formulations F1-F4 as described in Table 16 were subjected to photostability testing. Overall, twelve syringes (three each per formulation) were placed on the surface of a box covered with white printer paper 3.5 inches below the lamp source. Syringes were placed in numeric order as follows (1 2 3 4 1 2 3 4 1 2 3 4) about 1 inch apart. The end syringes (1 and 4) were each 5 inches from the ends of the lamp.

The light sources were two cool-white fluorescence lamps (GE Ecolux F20T12-CW-ECO, 20 W each) and two near-UV fluorescent lamps with spectral distributions from 320 to 400 nm, 20 W each. The exposure time at ambient temperature was 14 days for the cool-white fluorescent lamps and 88 hours for the near-UV lamps.

Agitation Studies

Three syringes for each of the different formulations to be tested were removed from refrigeration conditions and pooled in 15 mL Nunc conical tubes and individually secured to the platform of a Thermo Scientific MaxQ 2000 orbital shaker and agitated at 150 rpm for 24 hours under ambient light and temperature conditions.

Freeze-Thaw (F/T) Cycling Studies

Syringes for each of the different formulations to be tested, were removed from refrigeration conditions and pooled in 15 mL Nunc conical tubes. Pooled samples were then subjected to 5 cycles of freezing (−20° C.) and thawing (using ambient temperature water).

Study I: First Liquid Formulations Screen

An initial formulation screen for a liquid formulation of MOR6654B was set up testing e.g. different buffers, stabilizers, excipients and pH values. A few formulations were also investigated to gain experience for the primary packing selection and to gain experience on the stability of MOR6654B liquid formulation in the different types of PFS (Pre filled syringes).

Preparation of Samples

The formulations were produced using Drug Substance (MOR6654B) obtained from a CHO cell line expressing the afucosylated monoclonal antibody up-concentrated to 160 g/L in water. MOR6654B Drug Substance was mixed with an appropriate amount of excipient dilution solution, sterile filtered, filled aseptically into sterile 1 mL PFS (0.7 mL filling volume) or 6 mL glass vials (3.6 mL fill volume) and stoppered with Dalkyo D21-7S V10-F7-3WRS RB2-TR lyo stoppers. All the formulations tested were at 100 g/L of MOR6654B.

TABLE 5

List of formulations, First liquid formulation screen of MOR6654B (100 g/L) PP (Primary Packaging); HPbCD (hydroxyproyl-b-cyclodextrin)

| Form | pH | buffer 20 mM | stabilizer | surfactant | PP |
|---|---|---|---|---|---|
| 1 | 6.5 | Histidine | Trehalose 270 mM | Polysorbate 20 0.04% | PFS |
| 2 | 6.5 | Citrate | ArgHCl 150 mM | Poloxamer 188 0.3% | PFS |
| 3 | 6.5 | Histidine | Trehalose 270 mM | Polysorbate 20 0.04% | PFS |
| 4 | 7 | Succinate | ArgHCl 150 mM | Polysorbate 20 0.04% | PFS |
| 5 | 7 | Citrate | Trehalose 270 mM | None | PFS |
| 6 | 7 | Histidine | Mannitol 270 mM | Poloxamer 188 0.3% | PFS |
| 7 | 6 | Citrate | Mannitol 270 mM | Polysorbate 20 0.04% | PFS |
| 8 | 6.5 | Histidine | Trehalose 270 mM | Polysorbate 20 0.04% | PFS |
| 9 | 6 | Histidine | ArgHCl 150 mM | None | PFS |
| 10 | 6 | Succinate | Trehalose 270 mM | Poloxamer 188 0.3% | PFS |
| 11 | 6.5 | Succinate | Mannitol 270 mM | None | PFS |
| 12 | 6.5 | Succinate | Trehalose 270 mM | Polysorbate 20 0.04% | PFS |
| 13 | 6.5 | Histidine | Trehalose 270 mM | HPbCD 2.5 mM | PFS |
| 14 | 6.5 | Histidine | NaCl 150 mM | Polysorbate 20 0.04% | PFS |
| 15 | 6.5 | Histidine | Trehalose 270 mM | Polysorbate 20 0.04% | VIAL |
| 16 | 6.5 | Histidine | Trehalose 270 mM | Poloxamer 188 0.3% | VIAL |

Results
Tables of Results for Size Exclusion Chromatography (SEC-HPLC)

TABLE 6

Purity by SEC samples in freeze thaw stress

| Formulation | Aggregation products | Main peak | Degradation products |
|---|---|---|---|
| 1 | 0.52 | 99.38 | 0.10 |
| 2 | 0.59 | 99.31 | 0.10 |
| 3 | 0.51 | 99.39 | 0.10 |
| 4 | 0.62 | 99.29 | 0.08 |
| 5 | 0.62 | 99.29 | 0.10 |
| 6 | 1.92 | 97.94 | 0.13 |
| 7 | 1.26 | 98.66 | 0.08 |
| 8 | 0.53 | 99.36 | 0.10 |
| 9 | 0.56 | 99.35 | 0.10 |
| 10 | 0.64 | 99.28 | 0.08 |
| 11 | 1.75 | 98.15 | 0.10 |
| 12 | 0.56 | 99.38 | 0.07 |
| 13 | 0.51 | 99.40 | 0.09 |
| 14 | 0.72 | 99.19 | 0.08 |
| 15 | 0.56 | 99.35 | 0.09 |
| 16 | 0.56 | 99.36 | 0.09 |

TABLE 7

Purity by SEC samples in shaking stress

| Formulation | Aggregation products | Main peak | Degradation products |
|---|---|---|---|
| 1 | 0.51 | 99.37 | 0.12 |
| 2 | 0.60 | 99.31 | 0.09 |
| 3 | 0.52 | 99.38 | 0.10 |
| 4 | 0.68 | 99.23 | 0.09 |
| 5 | 0.73 | 99.16 | 0.11 |
| 6 | 0.70 | 99.18 | 0.12 |
| 7 | 0.65 | 99.25 | 0.10 |
| 8 | 0.54 | 99.35 | 0.11 |
| 9 | 0.53 | 99.37 | 0.10 |
| 10 | 0.64 | 99.27 | 0.09 |
| 11 | 0.64 | 99.25 | 0.10 |
| 12 | 0.58 | 99.30 | 0.13 |
| 13 | 0.53 | 99.37 | 0.10 |
| 14 | 0.62 | 99.25 | 0.13 |
| 15 | 0.57 | 99.31 | 0.12 |
| 16 | 0.58 | 99.30 | 0.12 |

TABLE 8

Purity by SEC samples in thermal stress (40° C.)

| Formulation | Aggregation products | Main peak | Degradation products |
|---|---|---|---|
| 1 | 1.09 | 95.84 | 3.07 |
| 2 | 1.05 | 95.93 | 3.02 |
| 3 | 1.13 | 95.72 | 3.15 |
| 4 | 1.34 | 95.22 | 3.44 |
| 5 | 2.06 | 94.06 | 3.88 |
| 6 | 1.58 | 94.77 | 3.65 |
| 7 | 1.33 | 95.75 | 2.92 |
| 8 | 1.13 | 95.75 | 3.12 |
| 9 | 0.90 | 95.89 | 3.21 |
| 10 | 1.24 | 95.78 | 2.98 |
| 11 | 1.45 | 95.48 | 3.07 |
| 12 | 1.14 | 95.81 | 3.05 |
| 13 | 1.02 | 95.90 | 3.08 |
| 14 | 1.21 | 95.63 | 3.17 |
| 15 | 1.32 | 94.75 | 3.92 |
| 16 | 1.51 | 93.56 | 4.93 |

TABLE 9

Purity by SEC for t0, and stability samples at 5° C.

| Form | Aggregation products T0 | Aggregation products 3 months at 5° C. | Aggregation products 6 months at 5° C. | Degradation products T0 | Degradation products 3 months at 5° C. | Degradation products 6 months at 5° C. |
|---|---|---|---|---|---|---|
| 1 | 0.46 | 0.53 | 0.54 | 0.1 | 0.09 | 0.12 |
| 2 | 0.54 | 0.62 | 0.61 | 0.09 | 0.07 | 0.11 |
| 3 | 0.46 | 0.56 | 0.53 | 0.09 | 0.09 | 0.12 |
| 4 | 0.61 | 0.77 | 0.76 | 0.08 | 0.07 | 0.12 |
| 5 | 0.59 | 0.79 | 0.76 | 0.1 | 0.08 | 0.13 |
| 6 | 0.63 | 0.75 | 0.69 | 0.08 | 0.08 | 0.14 |
| 7 | 0.59 | 0.67 | 0.57 | 0.08 | 0.05 | 0.11 |
| 8 | 0.5 | 0.59 | 0.48 | 0.1 | 0.08 | 0.12 |
| 9 | 0.5 | 0.57 | 0.47 | 0.1 | 0.08 | 0.12 |
| 10 | 0.6 | 0.67 | 0.51 | 0.08 | 0.06 | 0.12 |
| 11 | 0.57 | 0.71 | 0.55 | 0.09 | 0.08 | 0.12 |
| 12 | 0.52 | 0.61 | 0.45 | 0.09 | 0.06 | 0.13 |
| 13 | 0.51 | 0.57 | 0.42 | 0.11 | 0.05 | 0.11 |
| 14 | 0.55 | 0.65 | 0.49 | 0.07 | 0.04 | 0.13 |
| 15 | 0.51 | 0.61 | 0.43 | 0.1 | 0.09 | 0.13 |
| 16 | 0.53 | 0.64 | 0.44 | 0.09 | 0.07 | 0.14 |

TABLE 10

Purity by SEC for t0, and stability samples at 25° C.

| Form No. | Aggregation products T0 | Aggregation products 3 months at 25° C. | Aggregation products 6 months at 25° C. | Degradation products T0 | Degradation products 3 months at 25° C. | Degradation products 6 months at 25° C. |
|---|---|---|---|---|---|---|
| 1 | 0.46 | 0.8 | 0.56 | 0.1 | 1.41 | 2.47 |
| 2 | 0.54 | 0.91 | 0.54 | 0.09 | 1.37 | 2.3 |

TABLE 10-continued

Purity by SEC for t0, and stability samples at 25° C.

| Form No. | Aggregation products T0 | Aggregation products 3 months at 25° C. | Aggregation products 6 months at 25° C. | Degradation products T0 | Degradation products 3 months at 25° C. | Degradation products 6 months at 25° C. |
|---|---|---|---|---|---|---|
| 3 | 0.46 | 0.78 | 0.58 | 0.09 | 1.26 | 2.44 |
| 4 | 0.61 | 1.12 | 0.81 | 0.08 | 1.43 | 2.62 |
| 5 | 0.59 | 1.39 | 1.19 | 0.1 | 1.6 | 2.73 |
| 6 | 0.63 | 1.1 | 0.83 | 0.08 | 1.42 | 2.7 |
| 7 | 0.59 | 0.97 | 0.57 | 0.08 | 1.23 | 2.18 |
| 8 | 0.5 | 0.79 | 0.52 | 0.1 | 1.34 | 2.36 |
| 9 | 0.5 | 0.75 | 0.29 | 0.1 | 1.27 | 2.23 |
| 10 | 0.6 | 0.92 | 0.5 | 0.08 | 1.26 | 2.22 |
| 11 | 0.57 | 1.06 | 0.67 | 0.09 | 1.31 | 2.23 |
| 12 | 0.52 | 0.84 | 0.54 | 0.09 | 1.28 | 2.39 |
| 13 | 0.51 | 0.84 | 0.47 | 0.11 | 1.32 | 2.33 |
| 14 | 0.55 | 0.94 | 0.51 | 0.07 | 1.4 | 2.38 |
| 15 | 0.51 | 0.94 | 0.77 | 0.1 | 1.55 | 3.32 |
| 16 | 0.53 | 1.08 | 0.93 | 0.09 | 1.82 | 3.42 |

TABLE 11

Charge variants by CEX samples in freeze thaw stress

| Formulation | Acidic variants | Main peak | Basic variants |
|---|---|---|---|
| 1 | 5.18 | 65.42 | 29.40 |
| 2 | 5.10 | 66.21 | 28.69 |
| 3 | 4.97 | 66.01 | 29.01 |
| 4 | 5.27 | 65.34 | 29.40 |
| 5 | 5.35 | 64.79 | 29.86 |
| 6 | 5.23 | 65.78 | 28.99 |
| 7 | 5.38 | 65.60 | 29.02 |
| 8 | 5.24 | 67.21 | 27.55 |
| 9 | 5.02 | 64.24 | 30.74 |
| 10 | 5.56 | 65.18 | 29.26 |
| 11 | 5.50 | 65.04 | 29.45 |
| 12 | 5.19 | 66.32 | 28.49 |
| 13 | 5.45 | 65.06 | 29.49 |
| 14 | 5.43 | 66.04 | 28.54 |
| 15 | 5.33 | 66.18 | 28.49 |
| 16 | 5.24 | 66.11 | 28.65 |

TABLE 12

Charge variants by CEX samples in shaking stress

| Formulation | Acidic variants | Main peak | Basic variants |
|---|---|---|---|
| 1 | 5.09 | 66.35 | 28.56 |
| 2 | 5.03 | 66.83 | 28.13 |
| 3 | 5.05 | 66.98 | 27.97 |
| 4 | 5.07 | 66.60 | 28.33 |
| 5 | 5.17 | 65.47 | 29.36 |
| 6 | 5.34 | 66.70 | 27.97 |
| 7 | 5.36 | 66.63 | 28.01 |
| 8 | 5.11 | 66.95 | 27.94 |
| 9 | 4.78 | 66.45 | 28.77 |
| 10 | 4.99 | 67.25 | 27.76 |
| 11 | 5.12 | 66.21 | 28.67 |
| 12 | 5.21 | 67.18 | 27.60 |
| 13 | 5.41 | 66.40 | 28.19 |
| 14 | 5.05 | 67.29 | 27.66 |
| 15 | 5.14 | 66.70 | 28.16 |
| 16 | 5.15 | 66.84 | 28.01 |

TABLE 13

Charge variants by CEX samples in thermal stress (40° C.)

| Formulation | Acidic variants | Main peak | Basic variants |
|---|---|---|---|
| 1 | 13.41 | 59.24 | 27.35 |
| 2 | 12.00 | 61.63 | 26.37 |
| 3 | 14.43 | 58.54 | 27.03 |
| 4 | 13.59 | 60.20 | 26.21 |
| 5 | 14.40 | 58.18 | 27.42 |
| 6 | 15.36 | 58.63 | 26.01 |
| 7 | 14.83 | 58.99 | 26.18 |
| 8 | 14.10 | 59.34 | 26.55 |
| 9 | 12.70 | 58.92 | 28.38 |
| 10 | 15.17 | 58.64 | 26.19 |
| 11 | 14.09 | 58.86 | 27.05 |
| 12 | 14.31 | 59.15 | 26.54 |
| 13 | 14.54 | 58.97 | 26.49 |
| 14 | 12.22 | 61.15 | 26.62 |
| 15 | 15.01 | 58.21 | 26.79 |
| 16 | 16.54 | 56.43 | 27.03 |

TABLE 14

Charge variants by CEX for t0, and stability samples at 5° C.

| Form No. | Acidic variants T0 | Acidic variants 3 months at 5° C. | Acidic variants 6 months at 5° C. | Basic variants T0 | Basic variants 3 months at 5° C. | Basic variants 6 months at 5° C. |
|---|---|---|---|---|---|---|
| 1 | 4.19 | 6.13 | 14.43 | 30.56 | 25.39 | 20.14 |
| 2 | 4.73 | 5.66 | 14.35 | 30.18 | 26.33 | 20.81 |
| 3 | 4.73 | 6.33 | 14.9 | 29.48 | 26.66 | 20.48 |
| 4 | 4.76 | 5.71 | 14.08 | 29.71 | 26.16 | 21.53 |
| 5 | 4.8 | 5.91 | 14.47 | 30.69 | 27.66 | 20.82 |
| 6 | 4.97 | 6.22 | 15.73 | 29.1 | 26.14 | 21.2 |
| 7 | 4.68 | 5.5 | 14.33 | 29.15 | 25.69 | 21.45 |
| 8 | 4.75 | 5.99 | 14.98 | 29.12 | 25.91 | 20.77 |
| 9 | 4.71 | 5.54 | 14.13 | 30.48 | 25.89 | 21.24 |
| 10 | 4.78 | 5.83 | 14.55 | 29.38 | 26.11 | 21.12 |
| 11 | 4.89 | 5.82 | 14.04 | 30.24 | 26.39 | 21.3 |
| 12 | 4.74 | 6.2 | 14.52 | 28.29 | 25.8 | 20.98 |
| 13 | 5.04 | 6.26 | 16.13 | 30.22 | 25.75 | 21.43 |
| 14 | 5.02 | 5.7 | 14.62 | 28.86 | 25.26 | 21.38 |
| 15 | 5.02 | 5.9 | 16.87 | 29.02 | 25.81 | 22.59 |
| 16 | 5.17 | 6.01 | 16.92 | 29.07 | 25.48 | 22.52 |

TABLE 15

Charge variants by CEX for t0, and stability samples at 25° C.

| Form No. | Acidic variants T0 | Acidic variants 3 months at 25° C. | Acidic variants 6 months at 25° C. | Basic variants T0 | Basic variants 3 months at 25° C. | Basic variants 6 months at 25° C. |
|---|---|---|---|---|---|---|
| 1 | 4.19 | 7.75 | 27.71 | 30.56 | 24.44 | 21.16 |
| 2 | 4.73 | 6.81 | 22.26 | 30.18 | 25.64 | 20.38 |
| 3 | 4.73 | 6.81 | 24.95 | 29.48 | 24.38 | 20.28 |
| 4 | 4.76 | 8.02 | 24.73 | 29.71 | 24.96 | 20 |
| 5 | 4.8 | 7.67 | 28.55 | 30.69 | 23.86 | 21.46 |
| 6 | 4.97 | 7.36 | 25.94 | 29.1 | 24.86 | 18.62 |
| 7 | 4.68 | 7.05 | 31.1 | 29.15 | 23.96 | 20.23 |
| 8 | 4.75 | 7.85 | 27.67 | 29.12 | 24.73 | 20.93 |
| 9 | 4.71 | 7.72 | 29.52 | 30.48 | 24.65 | 19.3 |
| 10 | 4.78 | 7.87 | 27.61 | 29.38 | 24.76 | 20.33 |
| 11 | 4.89 | 8.7 | 36.3 | 30.24 | 23.58 | 19.85 |
| 12 | 4.74 | 7.24 | 25.53 | 28.29 | 24.91 | 20.58 |
| 13 | 5.04 | 7.41 | 24.77 | 30.22 | 24.14 | 19.91 |
| 14 | 5.02 | 7.75 | 29.63 | 28.86 | 25.37 | 21.95 |
| 15 | 5.02 | 8.09 | 28.7 | 29.02 | 24.56 | 20.01 |
| 16 | 5.17 | 8.18 | 32.26 | 29.07 | 24.94 | 22.16 |

Summary of Results, First Liquid Formulation Screen

Sixteen formulations of the monoclonal antibody, MOR6654B, were placed on stability for up to six months at 5° C. and 25° C. In addition, the same formulations were subjected to agitation stress, repeated F/T cycling and thermal stress (1 month at 40° C.). A wide variety of biophysical and biochemical analytical methods was used to determine if there were differences between the formulations in terms of stability. SEC data pointed to a difference in stability among the formulations tested. In the shaking stress samples, formulation 5 (pH 7 without surfactant) showed a higher increase in aggregation products, proving the beneficial effect of polysorbate. More severe increase in aggregation product was recorded upon freeze thaw stress in the mannitol and sodium chloride formulations.

The outcome of this first study can be summarized as follows: The preferred pH is 6.0. The non-ionic stabilizer tested, Trehalose, is beneficial to the formulation stability. Polysorbate 20 is beneficial to the stability of the formulation preventing formation of aggregates.

Study II: Second Liquid Formulation Screen
Formulation of Anti-BAFFR Antibodies

Three formulations (F1, F2, and F3) of MOR6654B with a high antibody concentration of 150 mg/mL and one formulation with a lower antibody concentration of 20 mg/mL (F4) were evaluated for stability. The four formulations F1, F2, F3 and F4 were filled into a 1.0 mL siliconized glass syringe and included buffer, sugar, surfactant and free amino acid as shown in Table 16.

TABLE 16

Composition of experimental formulations

| | MOR6654B | Buffer | Sugar | Surfactant | Amino acid |
|---|---|---|---|---|---|
| F1 | 150 mg/mL | 20 mM histidine; 6.0 | 220 mM sucrose | 0.04% polysorbate 20 | — |
| F2 | 150 mg/mL | 20 mM histidine; 6.0 | 220 mM trehalose | 0.04% polysorbate 20 | — |
| F3 | 150 mg/mL | 20 mM histidine; 6.0 | 120 mM sucrose | 0.04% polysorbate 20 | 50 mM arginine-HCl |
| F4 | 20 mg/mL | 20 mM histidine; 6.0 | 220 mM sucrose | 0.04% polysorbate 20 | — |

Samples of each formulation were prepared and tested for stability at three different temperatures. The four liquid formulations were placed under experimental storage conditions and tested for stability following storage at 2° C.-8° C. at time points 0 ($t_0$), and 2 month ($t_2$)
25° C. at time points 0 ($t_0$) and 2 month ($t_2$)
40° C. at time points 0 (t0), 1 ($t_1$) and 2 month ($t_2$)

In addition to storage at various temperatures, the formulations were subjected to a number of stress conditions, such as prolonged light exposure, agitation and multiple freeze-thaw (F1T) cycles. Each sample was analyzed using a variety of methods.

Results and Discussion, Second Formulation Screen

All four formulations were tested at the same time, depending on the stress condition. At time point zero (t0), measurements were made in duplicate, as were the measurements made after two months (t2). All other samples were only analyzed with single replicates. The more relevant results are reported below.

Nephelometry

Nephelometry is a turbidometric method used to detect the presence of soluble aggregates or to indicate opalescence. The output is listed in terms of nephelometric turbidity units (NTUs).

TABLE 17

Nephalometric turbidity units (NTUs)) for MOR6654B formulations stored at 40° C. for up to two months.

| | $t_0$ | 40° C. for 1 month | 40° C. for 2 month |
|---|---|---|---|
| F1 | 5.16/5.26 | 6.19 | 4.00/4.07 |
| F2 | 4.63/4.39 | 4.99 | 4.12/3.95 |
| F3 | 8.94/8.54 | 9.60 | 8.34/8.33 |
| F4 | 3.54/3.63 | 4.39 | 3.40/3.39 |

The nephelometry results show that the protein is quite physically stable, with no apparent change even after two months at 40° C.

Not surprising, storage at lower temperatures did not produce any appreciable change in the NTU levels for any of the formulations either (Table 18). Why formulation 3 exhibits a higher number of NTUs is not clear.

TABLE 18

Nephelometric turbidity units (NTUs)) for MOR6654B formulations stored at 4° C or 25° C. for two months.

| | $t_0$ | 2-8° C. for 2 month | 25° C. for 2 month |
|---|---|---|---|
| F1 | 5.16/5.26 | 4.56/4.48 | 4.10/3.65 |
| F2 | 4.63/4.39 | 5.56/4.09 | 3.43/3.39 |
| F3 | 8.94/8.54 | 8.11/7.95 | 9.57/8.55 |
| F4 | 3.54/3.63 | 3.43/3.47 | 2.98/2.76 |

TABLE 19

Nephelometric turbidity units (NTUs)) for MOR6654B formulations subjected to agitation stress (agit), multiple F/T cycles (F/T), and prolonged exposure to light (photo).

| | $t_0$ | Agit | F/T | Photo |
|---|---|---|---|---|
| F1 | 5.16/5.26 | 6.72 | 6.28 | 4.02 |
| F2 | 4.63/4.39 | 5.22 | 5.26 | 3.91 |
| F3 | 8.94/8.54 | 9.58 | 9.18 | 8.59 |
| F4 | 3.54/3.63 | 4.48 | 4.22 | 3.15 |

Finally, nephelometry of the samples subjected to stress conditions, such as agitation, multiple F/T cycles, and prolonged exposure to light revealed only small changes in any of the formulations for any of the stress conditions. For example, formulation 1 showed an increase of about 1.5 NTU upon agitation and approx. 1 NTU upon F/T stress. By comparison, the increase in formulation 2 was less than 1 NTU for either stress condition. Likewise, the lower concentration formulation 4, which also contains sucrose, shows a slight rise of about 1 NTU upon agitation.

High Pressure Liquid Chromatograph (HPLC) Measurements

Size Exclusion Chromatograph (SEC)

Three kinds of HPLC analyses were performed for these samples, starting with Size Exclusion Chromatography (SEC). There is a clear loss of monomer as measured by SEC for samples stored at 40° C. for one or two months (Table 20).

TABLE 20

Purity (in terms of percent monomer) by SEC-HPLC for MOR6654B samples stored at 40° C for up to two months.

| | $t_0$ | 40° C. for 1 month | 40° C. for 2 month |
|---|---|---|---|
| F1 | 99.74/99.78 | 92.71 | 92.08/92.27 |
| F2 | 99.64/99.60 | 93.51 | 92.39/92.61 |
| F3 | 99.77/99.76 | 93.26 | 92.43/92.32 |
| F4 | 99.67/99.53 | 93.80 | 93.58/92.87 |

There is a loss of about 7%-8% monomer as measured by SEC for samples stored at 40° C. for one or two month.

TABLE 21

Purity (in terms of percent monomer) by SEC-HPLC SEC for MOR6654B samples stored at 4° C and 25° C for two months.

| | $t_0$ | 2-8° C. for 2 month | 25° C. for 2 month |
|---|---|---|---|
| F1 | 99.74/99.78 | 99.62/99.63 | 99.35/99.58 |
| F2 | 99.64/99.60 | 99.61/99.59 | 99.50/99.35 |
| F3 | 99.77/99.76 | 99.58/99.57 | 99.18/99.26 |
| F4 | 99.67/99.53 | 99.60/99.57 | 99.26/99.42 |

For samples stored at lower temperature, there is no loss of monomer at 4° C. and only a small loss of approx. 1% at 25° C. When considering the effects of the stress conditions, there is a slight decrease in all formulations upon agitation and F/T cycling, but no real difference between formulations. Upon photolysis, there is also a small decrease in monomer content. Again, differences between formulations are not readily apparent.

TABLE 22

Nephelometric turbidity units (NTUs) for MOR6654B formulations subjected to agitation stress (agit), multiple F/T cycles (F/T), and prolonged exposure to light (photo).

| | $t_0$ | Agit | F/T | Photo |
|---|---|---|---|---|
| F1 | 99.74/99.78 | 99.29 | 98.86 | 98.94 |
| F2 | 99.64/99.60 | 99.04 | 98.96 | 98.86 |
| F3 | 99.77/99.76 | 98.85 | 98.98 | 98.44 |
| F4 | 99.67/99.53 | 99.01 | 98.93 | 98.68 |

While an examination of the overall monomer content is helpful, it may be more useful to consider the overall stability profile. The following tables have been prepared summarizing the percent of each peak observed at each site. For convenience, the peaks are ordered by their relative retention time (RRTs) to remove slight variations in run times.

TABLE 23

Overall stability profile as measured by SEC for MOR6654B samples stored at 40° C. for up to two months.

| Formulation | Rep | Time Point | RRT 0.81 | 0.84 | 0.88 | 0.91 | 0.95 | 1.00 | 1.07 | 1.22 | 1.38 | 1.58 |
|---|---|---|---|---|---|---|---|---|---|---|---|---|
| Formulation 1 | 1 | 0 | | | 0.13 | | | 99.74 | | 0.04 | 0.09 | |
| | 2 | 0 | | | 0.14 | | | 99.78 | | 0.03 | 0.04 | |
| Formulation 2 | 1 | 0 | | | 0.31 | | | 99.64 | | 0.05 | | |
| | 2 | 0 | | | 0.33 | | | 99.60 | | 0.07 | | |
| Formulation 3 | 1 | 0 | | | 0.17 | | | 99.78 | | 0.05 | 0.05 | |
| | 2 | 0 | | | 0.19 | | | 99.77 | | 0.05 | | |
| Formulation 4 | 1 | 0 | | | 0.12 | | | 99.71 | | | | 0.17 |
| | 2 | 0 | | | 0.17 | | | 99.59 | | 0.07 | | 0.17 |
| Formulation 1 | 1 | 1 | | 1.12 | | | | 92.85 | 5.35 | 0.68 | | |
| Formulation 2 | 1 | 1 | | 1.10 | | | | 93.98 | 4.43 | 0.49 | | |
| Formulation 3 | 1 | 1 | | 0.90 | | 0.07 | | 93.61 | 4.84 | 0.58 | | |
| Formulation 4 | 1 | 1 | | 0.78 | | | | 94.70 | 4.03 | 0.49 | | |
| Formulation 1 | 1 | 2 | 0.16 | | 0.18 | | | 92.08 | 6.40 | 1.18 | | |
| | 2 | 2 | 0.17 | | 0.21 | | | 92.27 | 6.31 | 1.05 | | |
| Formulation 2 | 1 | 2 | | | 0.44 | | | 92.39 | 6.05 | 1.12 | | |
| | 2 | 2 | | | 0.19 | | 0.25 | 92.61 | 5.94 | 1.01 | | |
| Formulation 3 | 1 | 2 | | | 0.14 | | 0.20 | 92.43 | 6.27 | 0.96 | | |
| | 2 | 2 | | | 0.17 | | 0.19 | 92.32 | 6.27 | 1.05 | | |
| Formulation 4 | 1 | 2 | | | 0.30 | 0.18 | | 93.58 | 4.79 | 1.15 | | |
| | 2 | 2 | | | 0.29 | 0.18 | | 92.87 | 5.39 | 1.26 | | |

There was no high molecular weight aggregate peak detected at t0 (Table 23), and only three impurities found, including on peak at RRT 0.88, which is presumably an oligomer of some type. Upon storage at 40° C. for one month or two months, there is a substantial decrease in monomer content, with most of the degradation products eluting later than the main peak (Table 23). This indicates that fragmentation is more problematic than aggregation for these formulations.

For samples heated at 25° C. for two months, there is very little loss in monomer (<1%) (Table 24). This suggests that the apparent activation energy for the primary degradation pathway is quite large, which would be consistent with hydrolytic degradation. The same two fragmentation peaks are seen at RRT 1.07 and 1.22, with the peak at 1.07 being quite a bit larger in all samples. In fact, the RRT 1.22 is so small in formulations 1 and 2, that they were not integrated in the runs. Otherwise, there are only the smallest differences between formulations stored at 25° C. when assayed by SEC.

TABLE 24

Overall stability profile as measured by SEC for MOR6654B samples stored at 25° C. for two months.

| Formulation 25 C. | Rep | Time Point | RRT 0.81 | 0.88 | 0.91 | 0.96 | 1.00 | 1.07 | 1.22 | 1.38 | 1.58 |
|---|---|---|---|---|---|---|---|---|---|---|---|
| Formulation 1 | 1 | 0 |  | 0.13 |  |  | 99.74 |  | 0.04 | 0.09 |  |
|  | 2 | 0 |  | 0.14 |  |  | 99.78 |  | 0.03 | 0.04 |  |
| Formulation 2 | 1 | 0 |  | 0.31 |  |  | 99.64 |  | 0.05 |  |  |
|  | 2 | 0 |  | 0.33 |  |  | 99.60 |  | 0.07 |  |  |
| Formulation 3 | 1 | 0 |  | 0.17 |  |  | 99.78 |  | 0.05 | 0.05 |  |
|  | 2 | 0 |  | 0.19 |  |  | 99.77 |  | 0.05 |  |  |
| Formulation 4 | 1 | 0 |  | 0.12 |  |  | 99.71 |  |  |  | 0.17 |
|  | 2 | 0 |  | 0.17 |  |  | 99.59 |  | 0.07 |  | 0.17 |
| Formulation 1 | 1 | 2 |  |  |  | 0.33 | 99.35 |  | 0.32 |  |  |
|  | 2 | 2 |  | 0.13 |  |  | 99.58 |  | 0.29 |  |  |
| Formulation 2 | 1 | 2 |  | 0.29 |  |  | 99.50 |  | 0.21 |  |  |
|  | 2 | 2 |  | 0.34 |  |  | 99.35 |  | 0.31 |  |  |
| Formulation 3 | 1 | 2 |  | 0.47 |  |  | 99.18 |  | 0.31 | 0.03 |  |
|  | 2 | 2 |  | 0.41 |  |  | 99.26 |  | 0.29 | 0.03 |  |
| Formulation 4 | 1 | 2 |  | 0.40 |  |  | 99.26 |  | 0.33 | 0.01 |  |
|  | 2 | 2 |  | 0.35 |  |  | 99.42 |  | 0.21 | 0.02 |  |

For samples stored at 4° C. for two months, there is virtually no loss in monomer seen by SEC at either site (Tables 23). The amounts of oligomer are nearly identical for all formulations.

When the different stress conditions are examined (agitation, F/T, and photostability testing), little degradation is seen by SEC. Agitation seems to cause no appreciable chemical degradation and slight increases in oligomer levels, as does repeated F/T cycling. All formulations perform roughly the same. Upon exposure to light, the SEC analyses indicate higher fragmentation levels for formulation 3 (Table 26).

TABLE 25

Overall stability profile as measured by SEC for MOR6654B samples stored at 4° C. for two months.

| Formulation 4 C | Rep | Time Point | RRT 0.81 | 0.84 | 0.88 | 0.91 | 1.00 | 1.07 | 1.22 | 1.38 | 1.58 |
|---|---|---|---|---|---|---|---|---|---|---|---|
| Formulation 1 | 1 | 0 |  |  | 0.13 |  | 99.74 |  | 0.04 | 0.09 |  |
|  | 2 | 0 |  |  | 0.14 |  | 99.78 |  | 0.03 | 0.04 |  |
| Formulation 2 | 1 | 0 |  |  | 0.31 |  | 99.64 |  | 0.05 |  |  |
|  | 2 | 0 |  |  | 0.33 |  | 99.60 |  | 0.07 |  |  |
| Formulation 3 | 1 | 0 |  |  | 0.17 |  | 99.78 |  | 0.05 | 0.05 |  |
|  | 2 | 0 |  |  | 0.19 |  | 99.77 |  | 0.05 |  |  |
| Formulation 4 | 1 | 0 |  |  | 0.12 |  | 99.71 |  |  |  | 0.17 |
|  | 2 | 0 |  |  | 0.17 |  | 99.59 |  | 0.07 |  | 0.17 |
| Formulation 1 | 1 | 2 |  |  | 0.32 |  | 99.62 |  | 0.06 |  |  |
|  | 2 | 2 |  |  | 0.32 |  | 99.63 |  | 0.05 |  |  |
| Formulation 2 | 1 | 2 |  |  | 0.34 |  | 99.61 |  | 0.05 |  |  |
|  | 2 | 2 |  |  | 0.35 |  | 99.59 |  | 0.06 |  |  |
| Formulation 3 | 1 | 2 |  |  | 0.35 |  | 99.58 |  | 0.07 |  |  |
|  | 2 | 2 |  |  | 0.36 |  | 99.57 |  | 0.07 |  |  |
| Formulation 4 | 1 | 2 |  |  | 0.34 |  | 99.60 |  | 0.05 |  |  |
|  | 2 | 2 |  |  | 0.37 |  | 99.57 |  | 0.06 |  |  |

TABLE 26

Overall stability profile as measured by SEC for MOR6654B formulations subjected to agitation stress (agit), multiple F/T cycles (f/t), and prolonged exposure to light (photo).

| Formulation | Rep | Time Point | RRT 0.81 | 0.88 | 0.95 | 1.00 | 1.07 | 1.22 | 1.29 | 1.38 | 1.40 | 1.58 |
|---|---|---|---|---|---|---|---|---|---|---|---|---|
| Formulation 1 | 1 | 0 | | 0.13 | | 99.74 | | 0.04 | | 0.09 | | |
| | 2 | 0 | | 0.14 | | 99.78 | | 0.03 | | 0.04 | | |
| Formulation 2 | 1 | 0 | | 0.31 | | 99.64 | | 0.05 | | | | |
| | 2 | 0 | | 0.33 | | 99.60 | | 0.07 | | | | |
| Formulation 3 | 1 | 0 | | 0.17 | | 99.78 | | 0.05 | | 0.05 | | |
| | 2 | 0 | | 0.19 | | 99.77 | | 0.05 | | | | |
| Formulation 4 | 1 | 0 | | 0.12 | | 99.71 | | | | | | 0.17 |
| | 2 | 0 | | 0.17 | | 99.59 | | 0.07 | | | | 0.17 |
| Formulation 1 | 1 | agit | | 0.69 | | 99.31 | | | | | | |
| Formulation 2 | 1 | agit | | 0.94 | | 99.06 | | | | | | |
| Formulation 3 | 1 | agit | | 0.98 | | 98.89 | | 0.11 | | 0.02 | | |
| Formulation 4 | 1 | agit | | 0.85 | | 99.15 | | | | | | |
| Formulation 1 | 1 | F/T | | 0.94 | | 98.85 | | 0.20 | | | | |
| | 2 | F/T | | 0.94 | | 98.91 | | 0.15 | | | | |
| Formulation 2 | 1 | F/T | | 0.90 | | 98.96 | | 0.13 | | | | |
| | 2 | F/T | | 0.90 | | 99.00 | | 0.09 | | | | |
| Formulation 3 | 1 | F/T | | 0.92 | | 98.99 | | 0.09 | | | | |
| | 2 | F/T | | 0.92 | | 98.99 | | 0.09 | | | | |
| Formulation 4 | 1 | F/T | | 0.79 | | 99.09 | | 0.12 | | | | |
| | 2 | F/T | | 0.79 | | 99.09 | | 0.10 | | | | |
| Formulation 1 | 1 | photo | | 0.77 | | 98.94 | | 0.25 | 0.04 | | | |
| | 2 | photo | | 0.80 | | 98.92 | | 0.25 | 0.04 | | | |
| Formulation 2 | 1 | photo | | 0.87 | | 98.86 | | 0.24 | 0.03 | | | |
| | 2 | photo | | 0.90 | | 98.84 | | 0.24 | 0.03 | | | |
| Formulation 3 | 1 | photo | | 0.61 | 0.26 | 98.44 | 0.09 | 0.57 | 0.03 | | | |
| | 2 | photo | | 0.62 | 0.25 | 98.49 | 0.10 | 0.52 | 0.02 | | | |
| Formulation 4 | 1 | photo | | 0.91 | | 98.68 | | 0.36 | 0.05 | | | |
| | 2 | photo | | 0.95 | | 98.56 | | 0.44 | 0.05 | | | |

RP HPLC

RP HPLC provides information on chemical degradation that might be occurring in the protein.

As chemical degradation seems to be occurring in MOR6654B, the RP HPLC analysis could be quite informative.

At $t_0$, all four formulations have a purity near 99.9% by RP HPLC.

After one month storage at 40° C., the purity decreases to approx. 96%, although the purity was markedly higher for formulation 4. The disparity in these values calls into questions whether this value is correct (Table 27).

At two months, all four formulations have decreased to about 94%, with little, if any, differences between the formulations.

TABLE 27

Purity of MOR6654B formulations determined by RP HPLC after storage at 40° C. for up to two months

| Form No | [protein] mg/mL | | t0 | | t1 | t2 | |
|---|---|---|---|---|---|---|---|
| 1 | 150 | sucrose | 99.86 | 99.89 | 96.09 | 93.97 | 94.01 |
| 2 | 150 | trehalose | 99.94 | 99.92 | 96.27 | 94.61 | 94.12 |
| 3 | 150 | sucrose/Arg | 99.93 | 99.93 | 95.82 | 94.13 | 94.30 |
| 4 | 20 | sucrose | 99.85 | 99.84 | 98.44 | 94.44 | 94.67 |

TABLE 28

Purity of MOR6654B formulations determined by RP HPLC after storage at 4° C. or 25° C. for two months

| Form No | [protein] mg/mL | | t0 | | t2 4° C. | | t2 25 C. | |
|---|---|---|---|---|---|---|---|---|
| 1 | 150 | sucrose | 99.86 | 99.89 | 96.92 | 96.85 | 96.63 | 96.61 |
| 2 | 150 | trehalose | 99.94 | 99.92 | 97.12 | 96.99 | 96.95 | 96.63 |
| 3 | 150 | sucrose/Arg | 99.93 | 99.93 | 96.88 | 96.99 | 96.49 | 96.46 |
| 4 | 20 | sucrose | 99.85 | 99.84 | 96.81 | 97.07 | 96.34 | 96.41 |

Storage at 25° C. for two months produces a decrease in purity by RP HPLC to ~96.5% (Table 28). The purity for samples stored at 4° C. was not that different, with purities near 97%. Again, all four formulations performed similarly.

Upon being subjected to stress conditions, the purity also decreases. For the agitation and F/T studies, the purity is about 97-98% for all of the formulations. However, upon exposure to light there is greater extent of degradation. The 150 mg/mL formulations decrease to about 94% while the 20 mg/mL formulation decreases all the way to <90%.

TABLE 29

Purity determined by RP HPLC of MOR6654B formulations subjected to agitation stress (agit), multiple F/T cycles (F/T), and prolonged exposure to light (photo).

| Form No | [protein] mg/mL | | t0 | | agit | F/T | photo |
|---|---|---|---|---|---|---|---|
| 1 | 150 | sucrose | 99.86 | 99.89 | 97.51 | 98.14 | 94.47 |
| 2 | 150 | trehalose | 99.94 | 99.92 | 97.46 | 97.67 | 94.45 |
| 3 | 150 | sucrose/Arg | 99.93 | 99.93 | 97.89 | 96.68 | 94.82 |
| 4 | 20 | sucrose | 99.85 | 99.84 | 96.74 | 97.29 | 89.51 |

As with SEC, it is helpful to examine the appearance of degradation products as well as consider the loss of the main peak. For samples stored at 40° C., the degradation profile is summarized in Table 30. Only one impurity is seen at t0, but multiple species are observed upon storage at elevated temperature. It appears that the relatively high purity seen for formulation 4 at t1 was simply due to not seeing the peak at RRT 1.19 (Table 30). Overall, there is very little difference between any of the four formulations regarding overall stability profiled as measured by RP HPLC.

TABLE 30

Degradation profile of MOR6654B formulations determined by RP HPLC after storage at 40° C. for one month (bold) and two months (italic)

| Formulation 40 C. | Rep | Time Point | 0.67 | 0.70 | 0.76 | 0.86 | 0.93 | 1.00 | 1.11 | 1.16 | 1.19 |
|---|---|---|---|---|---|---|---|---|---|---|---|
| Formulation 1 | 1 | 0 | | | | | 0.14 | 99.86 | | | |
| | 2 | 0 | | | | | 0.11 | 99.89 | | | |
| Formulation 2 | 1 | 0 | | | | | 0.11 | 99.89 | | | |
| | 2 | 0 | | | | | 0.21 | 99.79 | | | |
| Formulation 3 | 1 | 0 | | | | | 0.12 | 99.88 | | | |
| | 2 | 0 | | | | | 0.11 | 99.89 | | | |
| Formulation 4 | 1 | 0 | | | | | 0.15 | 99.85 | | | |
| | 2 | 0 | | | | | 0.16 | 99.84 | | | |
| Formulation 1 | 1 | 1 | | 0.01 | 0.04 | 1.35 | | 96.09 | | | 2.51 |
| Formulation 2 | 1 | 1 | | 0.01 | 0.02 | 1.44 | | 96.33 | | | 2.20 |
| Formulation 3 | 1 | 1 | | 0.02 | 0.06 | 1.70 | | 95.99 | | | 2.24 |
| Formulation 4 | 1 | 1 | | 0.01 | 0.03 | 1.52 | | 98.44 | | | |
| Formulation 1 | 1 | 2 | 0.04 | | | 2.72 | | 93.97 | 1.97 | 1.29 | |
| | 2 | 2 | 0.05 | | | 2.73 | | 94.01 | | 3.21 | |
| Formulation 2 | 1 | 2 | 0.02 | | | 2.67 | | 94.61 | | 2.70 | |
| | 2 | 2 | 0.06 | | | 2.73 | | 94.12 | 1.86 | 1.24 | |
| Formulation 3 | 1 | 2 | 0.08 | | | 2.87 | | 94.13 | 2.19 | 0.73 | |
| | 2 | 2 | 0.08 | | | 2.88 | | 94.30 | | 2.74 | |
| Formulation 4 | 1 | 2 | 0.05 | | | 2.89 | | 94.44 | 2.62 | | |
| | 2 | 2 | 0.05 | | | 2.72 | | 94.67 | 2.57 | | |

For samples stored at 25° C., there are two primary degradation products that elute after the main peak (Table 31). The stability profile for all four formulations is essentially the same at 25° C. when assayed using RP HPLC. Likewise, there a similar degradation profile for samples stored at 4° C. (Table 32).

TABLE 31

Degradation profile of MOR6654B formulations determined by RP HPLC after storage at 25° C. for t0 and two months

| Formulation 25 C. | Rep | Time Point | 0.67 | 0.76 | 0.86 | 0.93 | 1.00 | 1.11 | 1.16 | 1.19 |
|---|---|---|---|---|---|---|---|---|---|---|
| Formulation 1 | 1 | 0 | | | | 0.14 | 99.86 | | | |
|  | 2 | 0 | | | | 0.11 | 99.89 | | | |
| Formulation 2 | 1 | 0 | | | | 0.11 | 99.89 | | | |
|  | 2 | 0 | | | | 0.21 | 99.79 | | | |
| Formulation 3 | 1 | 0 | | | | 0.12 | 99.88 | | | |
|  | 2 | 0 | | | | 0.11 | 99.89 | | | |
| Formulation 4 | 1 | 0 | | | | 0.15 | 99.85 | | | |
|  | 2 | 0 | | | | 0.16 | 99.84 | | | |
| Formulation 1 | 1 | 2 | | | 0.64 | | 96.63 | 2.13 | | 0.60 |
|  | 2 | 2 | | | 0.56 | | 96.61 | 2.24 | | 0.59 |
| Formulation 2 | 1 | 2 | | | 0.55 | | 96.95 | 1.77 | | 0.72 |
|  | 2 | 2 | | | 0.56 | | 96.63 | 2.21 | | 0.60 |
| Formulation 3 | 1 | 2 | | | 0.63 | | 96.49 | 2.33 | | 0.55 |
|  | 2 | 2 | | | 0.65 | | 96.46 | 2.17 | | 0.72 |
| Formulation 4 | 1 | 2 | | | 0.55 | | 96.34 | 2.37 | | 0.74 |
|  | 2 | 2 | | | 0.54 | | 96.41 | 2.16 | | 0.88 |

TABLE 32

Degradation profile of MOR6654B formulations determined by RP HPLC after storage at 4° C. for up to two months

| Formulation 4 C. | Rep | Time Point | 0.67 | 0.76 | 0.86 | 0.93 | 1.00 | 1.11 | 1.16 | 1.19 |
|---|---|---|---|---|---|---|---|---|---|---|
| Formulation 1 | 1 | 0 | | | | 0.14 | 99.86 | | | |
|  | 2 | 0 | | | | 0.11 | 99.89 | | | |
| Formulation 2 | 1 | 0 | | | | 0.11 | 99.89 | | | |
|  | 2 | 0 | | | | 0.21 | 99.79 | | | |
| Formulation 3 | 1 | 0 | | | | 0.12 | 99.88 | | | |
|  | 2 | 0 | | | | 0.11 | 99.89 | | | |
| Formulation 4 | 1 | 0 | | | | 0.15 | 99.85 | | | |
|  | 2 | 0 | | | | 0.16 | 99.84 | | | |
| Formulation 1 | 1 | 2 | | | 0.25 | | 96.92 | 2.20 | 0.63 | |
|  | 2 | 2 | | | 0.24 | | 96.85 | 2.34 | 0.58 | |
| Formulation 2 | 2 | 2 | | | 0.17 | | 97.12 | 1.87 | 0.83 | |
|  | 2 | 2 | | | 0.23 | | 96.99 | 1.95 | 0.83 | |
| Formulation 3 | 1 | 2 | | | 0.16 | | 96.88 | 2.96 | | |
|  | 2 | 2 | | | 0.17 | | 96.99 | 2.84 | | |
| Formulation 4 | 1 | 2 | | | 0.23 | | 96.81 | 2.20 | 0.76 | |
|  | 2 | 2 | | | 0.16 | | 97.07 | 2.06 | 0.71 | |

When the samples are subjected to agitation, only one degradation product appears and the levels are similar in all of the samples (Table 33). Formulation 4 seems slightly less stable than the other three, possibly due to the lower protein concentration. Repeated F/T cycling also causes some modest damage as seen by RP HPLC, with the profile similar to that seen for agitation. This is seen repeatedly throughout the study, indicating that the interfacial sensitivity of this protein can be seen whether one does one test or the other. There does not appear to be a need to conduct both to assess the overall sensitivity to interfacial stress. Finally, exposure to light crates some early eluting species, which are likely fragments. Of the four formulations, the levels of these species are higher for formulation 3 (Table 33).

TABLE 33

Degradation profile determined by RP HPLC of MOR6654B formulations subjected to agitation stress (agit), multiple F/T cycles (F/T), and prolonged exposure to light (photo).

| Formulation Agitation | Rep | Condition | 0.68 | 0.75 | 0.87 | 0.93 | 0.96 | 1.00 | 1.10 | 1.16 | 1.24 | 1.29 |
|---|---|---|---|---|---|---|---|---|---|---|---|---|
| Formulation 1 | 1 | t0 | | | | | | 0.14 | 99.86 | | | |
|  | 2 | | | | | | | 0.11 | 99.89 | | | |
| Formulation 2 | 1 | t0 | | | | | | 0.11 | 99.89 | | | |
|  | 2 | | | | | | | 0.21 | 99.79 | | | |
| Formulation 3 | 1 | t0 | | | | | | 0.12 | 99.88 | | | |
|  | 2 | | | | | | | 0.11 | 99.89 | | | |
| Formulation 4 | 1 | t0 | | | | | | 0.15 | 99.85 | | | |
|  | 2 | | | | | | | 0.16 | 99.84 | | | |
| Formulation 1 | 1 | Agit | | | | 0.10 | | 98.07 | 1.83 | | | |
|  | 2 | | | | | 0.12 | | 96.96 | 2.92 | | | |

TABLE 33-continued

Degradation profile determined by RP HPLC of MOR6654B formulations subjected to agitation stress (agit), multiple F/T cycles (F/T), and prolonged exposure to light (photo).

| Formulation Agitation | Rep | Condition | 0.68 | 0.75 | 0.87 | 0.93 | 0.96 | 1.00 | 1.10 | 1.16 | 1.24 | 1.29 |
|---|---|---|---|---|---|---|---|---|---|---|---|---|
| Formulation 2 | 1 | Agit | | | | 0.29 | | 97.52 | 2.20 | | | |
| | 2 | | | | | | 0.13 | 97.40 | 2.47 | | | |
| Formulation 3 | 1 | Agit | | | | 0.10 | | 98.14 | 1.76 | | | |
| | 2 | | | | | | 0.11 | 97.64 | 2.25 | | | |
| Formulation 4 | 1 | Agit | | | | 0.11 | | 96.79 | | | 3.10 | |
| | 2 | | | | | | 0.11 | 96.68 | | | 3.21 | |
| Formulation 1 | 1 | F/T | | | | 0.17 | | 99.31 | | | | 0.51 |
| | 2 | | | | | | 0.23 | 96.96 | 2.81 | | | |
| Formulation 2 | 1 | F/T | | | | 0.26 | | 97.94 | 1.80 | | | |
| | 2 | | | | | | 0.27 | 97.40 | 2.33 | | | |
| Formulation 3 | 1 | F/T | | | | 0.17 | | 96.68 | 3.15 | | | |
| Formulation 4 | 1 | F/T | | | | 0.12 | | 97.11 | 2.78 | | | |
| | 2 | | | | | | 0.10 | 97.48 | 2.42 | | | |
| Formulation 1 | 1 | photo | 0.01 | | 0.62 | | 1.17 | 94.47 | 3.73 | | | |
| | 2 | | 0.01 | | 0.63 | | 1.42 | 96.93 | | 1.02 | | |
| Formulation 2 | 2 | photo | 0.01 | | 0.65 | | 1.52 | 94.45 | 3.38 | | | |
| | 2 | | 0.01 | | 0.68 | | 1.56 | 94.08 | 3.68 | | | |
| Formulation 3 | 1 | photo | 0.03 | | 1.36 | | 0.62 | 94.82 | 3.17 | | | |
| | 2 | | 0.03 | | 1.40 | | 0.87 | 93.98 | 3.73 | | | |
| Formulation 4 | 1 | photo | | 0.24 | 0.98 | | 6.05 | 89.51 | 3.23 | | | |
| | 2 | | | 0.25 | 0.93 | | 5.45 | 89.69 | 3.68 | | | |

Cationic Exchange Chromatography (CEX HPLC)

The third HPLC method used to evaluate the stability of the four MOR6654B formulations is cation exchange (CEX) chromatography. This method is intended to identify degradation products that differ in charge from the parent compound. Initially, all four formulations display a broad main peak that comprises about 98% of the total peak area (Table 34). Upon storage at 40° C. for one month, the main decreases to about 96%, with formulation 4 having a slightly higher purity (Table 34). After two months at 40° C., this has further decreased to about 95%, with formulation 1 showing the highest purity.

TABLE 34

Purity as determined by CEX HPLC of the MOR6654B formulations after storage at 40° C. for up to two months

| Form No | [protein] mg/mL | | t0 CEX | | t1 CEX | t2 CEX | |
|---|---|---|---|---|---|---|---|
| 1 | 150 | sucrose | 98.30 | 98.28 | 96.76 | 95.76 | 95.69 |
| 2 | 150 | trehalose | 98.35 | 98.28 | 96.62 | 95.17 | 95.31 |
| 3 | 150 | sucrose/Arg | 98.34 | 98.26 | 96.62 | 94.75 | 94.89 |
| 4 | 20 | sucrose | 98.30 | 98.22 | 97.31 | 95.39 | 95.13 |

TABLE 35

Purity as determined by CEX HPLC of the MOR6654B formulations after storage at 4° C. and 25° C. for two months

| Form No | [protein] mg/mL | | t0 CEX | | t2 4 C. CEX | | t2 25 C. CEX | |
|---|---|---|---|---|---|---|---|---|
| 1 | 150 | sucrose | 98.30 | 98.28 | 97.29 | 97.70 | 97.09 | 97.36 |
| 2 | 150 | trehalose | 98.35 | 98.28 | 97.45 | 97.35 | 97.31 | 97.20 |
| 3 | 150 | sucrose/Arg | 98.34 | 98.26 | 97.33 | 97.45 | 97.36 | 97.35 |
| 4 | 20 | sucrose | 98.30 | 98.22 | 97.05 | 97.38 | 97.42 | 97.46 |

For MOR6654B formulations stored for two months at 25° C., the purity decreases from >98% to ~97%, with formulation 4 being slightly, but only slightly, more stable (Table 35). When stored at 4° C. for the same amount of time, there is some loss in purity, similar to what was seen with the RP HPLC data. Again, it is no clear why there is roughly as much degradation in the 4° C. samples as in the 25° C., but the extent of degradation is small and all of the MOR6654B formulations behave approximately, the same.

TABLE 36

Purity as determined by CEX HPLC of the MOR6654B formulations subjected to agitation stress (agit), multiple F/T cycles (F/T), and prolonged exposure to light (photo).

| Form No | [protein] mg/mL | | t0 CEX | agit CEX | F/T CEX | photo CEX |
|---|---|---|---|---|---|---|
| 1 | 150 | sucrose | 98.30 98.28 | 97.59 | 97.54 | 98.91 |
| 2 | 150 | trehalose | 98.35 98.28 | 97.37 | 97.49 | 98.82 |
| 3 | 150 | sucrose/Arg | 98.34 98.26 | 97.33 | 97.96 | 98.41 |
| 4 | 20 | sucrose | 98.30 98.22 | 97.31 | 97.56 | 98.82 |

Upon agitation of repeated F/T cycling, there is some loss based on CEX HPLC, with all four formulations performing equally (Table 36). Prolonged exposure to light produced very little damage by CEX HPLC, in contrast to what has been seen with SEC and RP HPLC (Tables 26 and 29, respectively). This suggests that the degradation products generated by light do not differ in terms of charge from the parent compound.

Reducing Capillary Electrophoresis (rCE-SDS)

The capillary electrophoresis method here allows one to look at the extent of damage to the light chain (LC) and heavy chain (HC) of the antibody independently. In addition, it can provide an estimate of how much of the protein is not intact LC and HC, as indicated by the non-LC/HC content. At t0, there is approximately 25% LC and 70% HC by peak area, not correcting for the differences in size (Table 37), with the remainder (~5%) counted as non-LC/HC species (Table 38).

TABLE 37

Percentage of LC and HC as determined by rCE-SDS in MOR6654B formulations stored at 40° C. for up to two months

| Form No | [protein] mg/mL | | t0 | | | | t1 | | t2 | |
|---|---|---|---|---|---|---|---|---|---|---|
| | | | LC | HC | LC | HC | LC | HC | LC | HC |
| 1 | 150 | sucrose | 25.0 | 69.8 | 25.5 | 69.4 | 26.3 | 64.4 | 27.5 | 62.7 | 27.6 | 62.3 |
| 2 | 150 | trehalose | 25.9 | 69.4 | 26.0 | 69.2 | 26.9 | 64.7 | 27.0 | 62.3 | 27.0 | 61.3 |
| 3 | 150 | sucrose/Arg | 24.1 | 70.2 | 24.5 | 69.6 | 27.6 | 62.8 | 27.5 | 61.7 | 27.2 | 63.8 |
| 4 | 20 | sucrose | 24.9 | 67.8 | 24.9 | 67.9 | 27.3 | 67.5 | 26.5 | 65.0 | 27.0 | 63.6 |

After storage for one month at 40 C, the relative amounts of LC and HC have changed, with LC now accounting for ~27% and HC between 62 and 68% (Table 37). This indicates that HC is being lost. This is reflected in a marked increase in the amount of non-LC/HC species (Table 38), where these amounts have nearly doubled from pre-storage levels.

TABLE 38

Percentage of non-LC/HC species as determined by rCE-SDS in MOR6654B formulations stored at 40° C for up to two months

| Form No | [protein] | | t0 non-LC/HC | t1 non-LC/HC | t2 non-LC/HC |
|---|---|---|---|---|---|
| 1 | 150 | sucrose | 5.2 | 9.3 | 9.9 |
| 2 | 150 | trehalose | 4.8 | 8.4 | 11.2 |
| 3 | 150 | sucrose/Arg | 5.8 | 9.6 | 9.9 |
| 4 | 20 | sucrose | 7.3 | 5.2 | 9.0 |

By the end of two months, there is about 10% (or more) of the non-LC/HC species. These data suggest that formulation 4 is the most robust, with the smallest percent increase in non-LC/HC levels.

TABLE 39

Percentage of LC and HC as determined by rCE-SDS in MOR6654B formulations stored at 4° C. for two months

| Form No | [protein] mg/mL | | t0 | | | | t2 4 C. | | | | |
|---|---|---|---|---|---|---|---|---|---|---|---|
| | | | LC | HC | LC | HC | LC | HC | LC | HC | non-LC/HC |
| 1 | 150 | sucrose | 25.0 | 69.8 | 25.5 | 69.4 | 26.4 | 66.2 | 26.7 | 66.8 | 7.0 |
| 2 | 150 | trehalose | 25.9 | 69.4 | 26.0 | 69.2 | 27.3 | 68.7 | 27.3 | 67.9 | 4.4 |
| 3 | 150 | sucrose/Arg | 24.1 | 70.2 | 24.5 | 69.6 | 27.7 | 67.3 | 26.9 | 66.3 | 5.9 |
| 4 | 20 | sucrose | 24.9 | 67.8 | 24.9 | 67.9 | 25.8 | 67.6 | 25.9 | 67.3 | 6.7 |

When samples are stored at 4° C., there is still some degradation seen by rCE-SDS, as the LC levels rise form ~25% to ~27% (Table 39). In this case, formulation 2 is the most stable with little increase in the amounts of the non-LC/HC species.

TABLE 40

Percentage of LC and HC as determined by rCE-SDS in MOR6654B formulations stored at 25° C. for two months

| Form No | [protein] mg/mL | | t0 | | | | t2 25 C. | | | | |
|---|---|---|---|---|---|---|---|---|---|---|---|
| | | | LC | HC | LC | HC | LC | HC | LC | HC | non-LC/HC |
| 1 | 150 | sucrose | 25.0 | 69.8 | 25.5 | 69.4 | 27.9 | 67.4 | 28.0 | 67.5 | 4.6 |
| 2 | 150 | trehalose | 25.9 | 69.4 | 26.0 | 69.2 | 27.9 | 66.1 | 27.8 | 67.5 | 5.3 |
| 3 | 150 | sucrose/Arg | 24.1 | 70.2 | 24.5 | 69.6 | 26.4 | 67.5 | 26.9 | 66.0 | 6.6 |
| 4 | 20 | sucrose | 24.9 | 67.8 | 24.9 | 67.9 | 26.1 | 68.0 | 26.7 | 68.0 | 5.6 |

When stored at 25° C. for two months, there is a comparable increase in LC and decrease in HC content (Table 40). The levels of non-LC/HC species do rise, but nearly as much as for the 40 C samples. Of these, formulation 3 appears to have the poorest stability, but the differences are small.

TABLE 41

Percentage of LC and HC as determined by rCE-SDS in MOR6654B formulations subjected to agitation stress (agit), multiple F/T cycles (F/T), and prolonged exposure to light (photo).

| | | | agit | | | F/T | | | photo | | |
|---|---|---|---|---|---|---|---|---|---|---|---|
| Form No | [protein] mg/mL | | LC | HC | non-LC/HC | LC | HC | non-LC/HC | LC | HC | non-LC/HC |
| 1 | 150 | sucrose | 28.3 | 67.2 | 4.5 | 28.7 | 67.6 | 3.7 | 27.3 | 66.2 | 6.5 |
| 2 | 150 | trehalose | 28.2 | 68.3 | 3.5 | 27.9 | 67.7 | 4.4 | 27.0 | 66.1 | 6.9 |
| 3 | 150 | sucrose/ Arg | 28.3 | 68.4 | 3.3 | 27.6 | 69.3 | 3.1 | 26.6 | 66.1 | 7.3 |
| 4 | 20 | sucrose | 26.9 | 69.1 | 4.0 | 26.9 | 69.5 | 3.6 | 26.2 | 64.6 | 9.2 |

The final set of samples to be analyzed by rCE-SDS was those subjected to the three different stress conditions (Table 41). When samples are agitated or exposed to F/T cycling, there is no appreciable increase in non-LC/HC species for any for the four MOR6654B formulations. This is consistent with the other findings, that MOR6654B in these formulations is not very sensitive to interfacial stress. It also reinforces the idea that these two tests provide comparable assessments of interfacial stability. Prolonged exposure to light did result in some loss of HC and rise in the non-LC/HC levels (Table 41). Of these formulations, formulation 4 showed the biggest changes.

Microflow Imaging (MFI)

Over the last few years there has been an increased focus on the levels of sub-visible particles in injectable protein products. As a result, a number of different analytical methods have been developed. One of the most widely known is microflow imaging (MFI). This technique was used to measure the sub-visible particle content (in terms of particles per mL) within different size ranges. While data was collected up to 100 um in terms of size, only data up to 25 um is presented. The reproducibility of the MFI data is very good. The average relative standard deviation for duplicate measurements is about 5%.

Often, data summarized for MFI report only the total particle count (in particles per mL), but this can be misleading, as the numbers are dominated by particles being counted in the 1-2 um size range. In this size range, silicone oil and air bubbles are prominent, and skew the counting away form protein-based particles. While these numbers are provided, it is best to look at particles larger than 2 um, possibly greater than 5 um in size. Also, for samples reporting averages and standard deviations, these are the results of duplicate runs.

When stored at 40° C., the sub-visible particle count does rise for all of the formulations (Table 42). Of particular note is formulation 4, where the total particle count is less than 5000 particles per mL at t0, much lower than for the other higher concentration, formulations. After one month, all of the formulations now exceed 20000 particles per mL, although the increase for formulation 3 is quite small (Table 42). At the two months, only formulation 2 is less than 30000 particles per mL. The difference is even more striking for particles from 2-5 um (where this formulation contains less than 5000 particles per mL) and 5-10 um, where the levels are less than 1000 particles per mL, with only formulation 1 being close in terms of the total amount of sub-visible particles present.

TABLE 42

Sub-visible content (in particles/mL) as measured using MFI for MOR6654B formulations stored at 40° C. for one month (in bold) and two months (in italics). Samples at t1 were not assayed in duplicate. Otherwise, the values reported are averages ± one standard deviation.

| Form No | [protein] mg/mL | Excipient | total | 1-2 um | 2-5 um | 5-10 um | 10-25 um |
|---|---|---|---|---|---|---|---|
| 1 | 150 | sucrose | 24137 ± 486 | 18257 ± 391 | 4968 ± 33 | 518 ± 6 | 78 ± 16 |
| 2 | 150 | trehalose | 12614 ± 660 | 9580 ± 661 | 2298 ± 64 | 568 ± 47 | 148 ± 10 |
| 3 | 150 | sucrose/ Arg | 33374 ± 975 | 23593 ± 718 | 8554 ± 174 | 1134 ± 88 | 82 ± 5 |
| 4 | 20 | sucrose | 4130 ± 28 | 2463 ± 134 | 1197 ± 15 | 441 ± 76 | 26 ± 14 |
| 1 | 150 | sucrose | 46508 | 36658 | 7768 | 1684 | 326 |
| 2 | 150 | trehalose | 22154 | 14920 | 5153 | 1867 | 214 |
| 3 | 150 | sucrose/ Arg | 34800 | 22990 | 9791 | 1926 | 82 |
| 4 | 20 | sucrose | 27372 | 15663 | 9660 | 1943 | 98 |
| *1* | *150* | *sucrose* | *35130 ± 2897* | *21931 ± 1725* | *8703 ± 544* | *3793 ± 596* | *683 ± 34* |
| *2* | *150* | *trehalose* | *24843 ± 3887* | *19692 ± 3789* | *4246 ± 39* | *757 ± 21* | *107 ± 1* |
| *3* | *150* | *sucrose/ Arg* | *46220 ± 3152* | *33038 ± 849* | *10853 ± 1957* | *2000 ± 110* | *239 ± 109* |
| *4* | *20* | *sucrose* | *51835 ± 1703* | *33847 ± 905* | *14942 ± 74* | *2411 ± 6* | *127 ± 11* |

TABLE 43

Sub-visible content (in particles/mL) as measured using MFI for MOR6654B formulations stored at 25° C. for two months (in bold). The values reported are averages ± one standard deviation.

| Form No | [protein] mg/mL | Excipient | total | 1-2 um | 2-5 um | 5-10 um | 10-25 um |
|---|---|---|---|---|---|---|---|
| 1 | 150 | sucrose | 24137 ± 486 | 18257 ± 391 | 4968 ± 33 | 518 ± 6 | 78 ± 16 |
| 2 | 150 | trehalose | 12614 ± 660 | 9580 ± 661 | 2298 ± 64 | 568 ± 47 | 148 ± 10 |
| 3 | 150 | sucrose/Arg | 33374 ± 975 | 23593 ± 718 | 8554 ± 174 | 1134 ± 88 | 82 ± 5 |
| 4 | 20 | sucrose | 4130 ± 28 | 2463 ± 134 | 1197 ± 15 | 441 ± 76 | 26 ± 14 |
| 1 | 150 | sucrose | 21362 ± 600 | 14928 ± 192 | 5420 ± 648 | 907 ± 124 | 101 ± 20 |
| 2 | 150 | trehalose | 35948 ± 1900 | 24189 ± 2258 | 9257 ± 252 | 2416 ± 609 | 70 ± 13 |
| 3 | 150 | sucrose/Arg | 67603 ± 1743 | 49362 ± 2758 | 12381 ± 154 | 4303 ± 282 | 1243 ± 560 |
| 4 | 20 | sucrose | 48163 ± 2420 | 31446 ± 950 | 15394 ± 1356 | 1240 ± 126 | 83 ± 13 |

When MOR6654B samples are stored at 25° C. for two months, there is an increase in sub-visible particles in all formulations, although the increase in formulation 1 is very small (Table 43). For formulation 1, there is only a modest increase in particles from 5 to 10 um in size. Otherwise, there is virtually no change. Meanwhile, there is a sizable increase in all of the other formulations, especially in the 2 to 25 um size ranges. In particular, formulations 3 and 4 show significant increases in most size range bins.

are large increases only for the photostability samples (Table 44). Both agitation and F/T cycling cause only small to modest increases in particle levels, especially if one ignores particles below 2 um. On the other hand, prolonged light exposure does cause sub-visible particle formation to increases sizably (Table 44). This is particularly true for formulations 3 and 4. By comparison, formulation 1 shows almost no change in the overall sub-visible particle burden.

TABLE 44

Sub-visible content (in particles/mL) as measured using MFI for MOR6654B formulations subjected to agitation stress (in bold), multiple F/T cycles (in italics), and prolonged exposure to light (underlined). The reported values for t0 are averages ± one standard deviation.

| Form No | [protein] mg/mL | Excipients | total | 1-2 um | 2-5 um | 5-10 um | 10-25 um |
|---|---|---|---|---|---|---|---|
| 1 | 150 | Sucrose/PS20/His | 24137 ± 486 | 18257 ± 391 | 4968 ± 33 | 518 ± 6 | 78 ± 16 |
| 2 | 150 | trehalose/PS20/His | 12614 ± 660 | 9580 ± 661 | 2298 ± 64 | 568 ± 47 | 148 ± 10 |
| 3 | 150 | sucrose/Arg/PS20/His | 33374 ± 975 | 23593 ± 718 | 8554 ± 174 | 1134 ± 88 | 82 ± 5 |
| 4 | 20 | sucrose/PS20/His | 4130 ± 28 | 2463 ± 134 | 1197 ± 15 | 441 ± 76 | 26 ± 14 |
| 1 | 150 | sucrose/PS20/His | 22306 | 14913 | 6288 | 1071 | 33 |
| 2 | 150 | trehalose/PS20/His | 35220 | 21637 | 9932 | 3345 | 301 |
| 3 | 150 | sucrose/Arg/PS20/His | 26857 | 16889 | 7264 | 2428 | 220 |
| 4 | 20 | sucrose/PS20/His | 10528 | 6511 | 3355 | 576 | 85 |
| *1* | *150* | *sucrose/PS20/His* | *35027* | *26159* | *7278* | *1343* | *226* |
| *2* | *150* | *trehalose/PS20/His* | *23502* | *17580* | *4856* | *979* | *89* |
| *3* | *150* | *sucrose/Arg/PS20/His* | *21686* | *15257* | *5256* | *1104* | *66* |
| *4* | *20* | *sucrose/PS20/His* | *9667* | *6078* | *2198* | *1340* | *45* |
| <u>1</u> | 150 | <u>sucrose/PS20/His</u> | <u>25417</u> | <u>18711</u> | <u>5723</u> | <u>864</u> | <u>102</u> |
| <u>2</u> | 150 | <u>trehalose/PS20/His</u> | <u>29238</u> | <u>22107</u> | <u>6160</u> | <u>823</u> | <u>147</u> |
| <u>3</u> | 150 | <u>sucrose/Arg/PS20/His</u> | <u>186398</u> | <u>167017</u> | <u>16314</u> | <u>2790</u> | <u>270</u> |
| <u>4</u> | 20 | <u>sucrose/PS20/His</u> | <u>46159</u> | <u>29359</u> | <u>14428</u> | <u>1224</u> | <u>131</u> |

His (histidine);
P20 (polysorbate 20);
Arg (arginine)

For MOR6654B formulations stored at 4° C. for two months there is little change in the sub-visible particle levels. Formulation 1 shows only a small increase in particles from 5-10 mm, with slight decrease in all of the other size ranges. Formulation 2 shows only small increases across the different size ranges, while formulation 3 displays small decreases in the overall particle levels. By comparison, formulation 4, which started with a very low sub-visible particle burden (barely above that of pure water), shows a significant increase in the particle per mL in all size ranges.

When MOR6654B formulations are subjected to the stress conditions of agitation, F/T cycling and light exposure, there Colorimetry The last analytical method that was used in this stability study was colorimetry. At t0, the four formulations all display a brown color (Table 45), with a slightly different color intensity for the more dilute formulation (formulation 4). Incubation at 40° C. for one or two months leads to little change in color, although formulation 4 does show some small changes (Table 45). When stored at lower temperatures, there is little, if any, change in color (Table 46). When subjected to any of the stress conditions, the color stays the same as well (Table 47).

TABLE 45

Color of the MOR6654B formulations stored at 40° C. for up to two months

| Form No | [protein] mg/mL | | t0 | | t1 | | t2 | |
|---|---|---|---|---|---|---|---|---|
| 1 | 150 | sucrose | B6 | B7 | B6 | B6 | B6 | B6 |
| 2 | 150 | trehalose | B7 | B7 | B7 | B6 | B6 | B6 |
| 3 | 150 | sucrose/Arg | B6 | B6 | B6 | B6 | B6 | B6 |
| 4 | 20 | sucrose | B8 | B8 | BY7 | BY7 | B7 | B6 |

TABLE 46

Color of the MOR6654B formulations stored at 4° C. and 25° C. for zero and two months

| Form No | [protein] mg/ml | | t0 | | t2 4° C. | | t2 25° C. | |
|---|---|---|---|---|---|---|---|---|
| 1 | 150 | sucrose | B6 | B7 | B7 | B7 | B6 | B6 |
| 2 | 150 | trehalose | B7 | B7 | B7 | B7 | B7 | B7 |
| 3 | 150 | sucrose/Arg | B6 | B6 | B6 | B6 | B6 | B6 |
| 4 | 20 | sucrose | B8 | B8 | B8 | B9 | B8 | B8 |

TABLE 47

Color of the MOR6654B formulations subjected to agitation stress (agit), multiple F/T cycles (F/T), and prolonged exposure to light (photo).

| Form No | [protein] mg/ml | | t0 | | agit | | F/T | | photo | |
|---|---|---|---|---|---|---|---|---|---|---|
| 1 | 150 | sucrose | B6 | B7 | B7 | B7 | B6 | B7 | B6 | B6 |
| 2 | 150 | trehalose | B7 | B7 | B7 | B7 | B7 | B7 | B6 | B6 |
| 3 | 150 | sucrose/Arg | B6 | B6 | B6 | B6 | B6 | B6 | B6 | B6 |
| 4 | 20 | sucrose | B8 | B8 | B8 | B8 | B8 | B8 | B7 | B7 |

SUMMARY

A wide variety of biophysical and biochemical analytical methods was used to determine if there were differences between the formulations in terms of stability. Among the formulations selected for the second screen, little difference was seen using many of the analytical techniques. Only storage at 40° C. and prolonged exposure to light caused any significant amount of degradation. While all four formulations were very similar in terms of their stability profile, formulation 1 (150 mg/mL MOR6654B, 220 mM sucrose, 20 mM histidine, 0.04% polysorbate 20, pH 6.0) showed the least propensity to degrade overall as determined by this battery of analytical methods. Formulation 1 was more stable in thermal and light stress conditions, less prone to degradation and was also more stable in terms of particles formation in the sub-visible range.

The invention claimed is:

1. An aqueous composition having a pH of 6.0 and comprising a hypofucosylated or non-fucosylated anti-B-cell Activating Factor Receptor (BAFFR) antibody wherein the antibody has a concentration of 150 mg/mL and wherein said anti-BAFFR antibody comprises heavy chain CDR1, CDR2 and CDR3 of SEQ ID NOs: 3, 4 and 5 respectively, and light chain CDR1, CDR2 and CDR3 of SEQ ID NOs: 6, 7 and 8 respectively, and (a) (i) 220 mM sucrose as a stabilizer,
   (ii) 20 mM histidine as a buffering agent,
   (iii) 0.04% polysorbate 20 as a surfactant; or (b) (i) 220 mM trehalose as a stabilizer,
   (ii) 20 mM histidine as a buffering agent,
   (iii) 0.04% polysorbate 20 as a surfactant; or (c) (i) 120 mM sucrose as a stabilizer,
   (ii) 20 mM histidine as a buffering agent,
   (iii) 0.04% polysorbate 20 as a surfactant, and
   (iv) 50 mM arginine.

2. The aqueous composition of claim 1, wherein the hypofucosylated or non-fucosylated anti-BAFFR antibody comprises a $V_H$ domain comprising the amino acid sequence of SEQ ID NO: 1 and a $V_L$ domain comprising the amino acid sequence of SEQ ID NO: 2.

3. The aqueous composition of claim 1, wherein the hypofucosylated or non-fucosylated anti-BAFFR antibody comprises a heavy chain region comprising the amino acid sequence of SEQ ID NO: 9 and a light chain region comprising the amino acid sequence of SEQ ID NO: 10.

4. A delivery device comprising the aqueous composition of claim 1.

5. A pre-filled syringe comprising the aqueous composition of claim 1.

* * * * *